United States Patent
Coates et al.

(10) Patent No.: US 9,851,295 B2
(45) Date of Patent: Dec. 26, 2017

(54) OPTICAL DEVICES FOR FLUID SENSING AND METHODS THEREFOR

(71) Applicant: Measurement Specialities, Inc., Hampton, VA (US)

(72) Inventors: John Coates, Newtown, CT (US); Robert Qualls, Carmel, IN (US)

(73) Assignee: MEASUREMENT SPECIALTIES, INC., Hampton, VA (US)

( * ) Notice: Subject to any disclaimer, the term of this patent is extended or adjusted under 35 U.S.C. 154(b) by 0 days.

(21) Appl. No.: 14/947,156

(22) Filed: Nov. 20, 2015

(65) Prior Publication Data

US 2016/0076995 A1    Mar. 17, 2016

Related U.S. Application Data

(62) Division of application No. 14/124,601, filed as application No. PCT/US2012/041431 on Jun. 7, 2012, now Pat. No. 9,322,773.

(60) Provisional application No. 61/520,308, filed on Jun. 7, 2011.

(51) Int. Cl.
| | |
|---|---|
| G01N 21/35 | (2014.01) |
| G01F 23/292 | (2006.01) |
| G01N 21/3504 | (2014.01) |
| G01N 21/3577 | (2014.01) |
| G01N 21/31 | (2006.01) |
| G01N 21/94 | (2006.01) |
| G01N 33/22 | (2006.01) |
| G01N 33/28 | (2006.01) |
| G01N 21/85 | (2006.01) |
| G01N 21/27 | (2006.01) |

(52) U.S. Cl.
CPC .......... *G01N 21/35* (2013.01); *G01F 23/292* (2013.01); *G01N 21/31* (2013.01); *G01N 21/3504* (2013.01); *G01N 21/3577* (2013.01); *G01N 21/94* (2013.01); *G01N 33/22* (2013.01); *G01N 33/28* (2013.01); *G01N 21/274* (2013.01); *G01N 21/314* (2013.01); *G01N 21/3151* (2013.01); *G01N 21/8507* (2013.01); *G01N 2021/3148* (2013.01); *G01N 2021/3181* (2013.01); *G01N 2021/8514* (2013.01); *G01N 2201/062* (2013.01); *G01N 2201/0627* (2013.01)

(58) Field of Classification Search
CPC .... G01N 21/35; G01N 21/31; G01N 21/3504; G01N 21/3577
See application file for complete search history.

(56) References Cited

U.S. PATENT DOCUMENTS

| | | |
|---|---|---|
| 3,120,125 A | 2/1964 | Vasel |
| 3,384,885 A | 5/1968 | Forbush |
| 3,766,395 A | 10/1973 | Keir |
| 3,818,470 A | 6/1974 | Hirsbrunner et al. |
| 3,864,577 A | 2/1975 | Pellett et al. |
| 3,872,315 A | 3/1975 | Boll |
| 3,908,378 A | 9/1975 | Wolfe et al. |
| 4,155,013 A | 5/1979 | Spiteri |
| 4,201,914 A | 5/1980 | Perren |
| 4,242,590 A | 12/1980 | von Tluck |
| 4,286,464 A | 9/1981 | Tauber et al. |
| 4,287,427 A * | 9/1981 | Scifres ............... G01F 23/2922 250/577 |
| 4,354,180 A | 10/1982 | Harding |
| 4,427,293 A | 1/1984 | Harmer |
| 4,443,699 A | 4/1984 | Keller |
| 4,609,628 A | 9/1986 | Aschenbeck |
| 4,713,552 A | 12/1987 | Denis et al. |
| 4,840,137 A | 6/1989 | Beauvais et al. |
| 4,938,590 A | 7/1990 | Ishida |
| 4,961,069 A | 10/1990 | Tsaprazis |
| 4,994,682 A | 2/1991 | Woodside |
| 4,998,022 A | 3/1991 | Tregay |
| 5,048,952 A | 9/1991 | Miyata et al. |
| 5,066,533 A | 11/1991 | America et al. |
| 5,159,834 A | 11/1992 | Eisele |
| 5,291,031 A | 3/1994 | MacDonald et al. |
| 5,452,083 A | 9/1995 | Wilks, Jr. |
| 5,708,860 A | 1/1998 | Nonaka et al. |
| 5,770,156 A | 6/1998 | Dosoretz et al. |

(Continued)

FOREIGN PATENT DOCUMENTS

| | | |
|---|---|---|
| CN | 101113921 A | 1/2008 |
| EP | 0639757 A1 | 2/1995 |

(Continued)

OTHER PUBLICATIONS

International Search Report dated Nov. 8, 2012 for related Application No. PCT/US12/41431.

(Continued)

*Primary Examiner* — David Porta
*Assistant Examiner* — Mindy Vu
(74) *Attorney, Agent, or Firm* — Howard IP Law Group, PC

(57) ABSTRACT

An optical spectral sensing device for determining at least one property of a fluid. The device has an elongated porous body, a first end and a second end, a solid-state optical emitter at the first end of the body oriented to emit radiation toward the second end of the body, and a solid-state optical detector at the second end of the body oriented to detect radiation emitted by the optical emitter and to output a signal responsive to absorption of radiation. The device is configured to determine depth of a fluid based on the signal output by the optical detector.

15 Claims, 17 Drawing Sheets

(56) References Cited

U.S. PATENT DOCUMENTS

| | | | |
|---|---|---|---|
| 5,826,113 A | 10/1998 | Nonaka | |
| 5,880,480 A | 3/1999 | Ellinger et al. | |
| 5,942,269 A | 8/1999 | Casey et al. | |
| 5,975,665 A | 11/1999 | Torigoe et al. | |
| 6,009,794 A | 1/2000 | Casey et al. | |
| 6,057,772 A | 5/2000 | Burkett | |
| 6,333,512 B1 | 12/2001 | Wirthlin | |
| 6,363,784 B1 | 4/2002 | Gregory | |
| 6,365,908 B1 | 4/2002 | Waigel et al. | |
| 6,448,573 B1 | 9/2002 | Benton | |
| 6,517,512 B1 | 2/2003 | Bock et al. | |
| 6,531,708 B1 | 3/2003 | Malmstrom et al. | |
| 6,555,837 B2 | 4/2003 | Benton | |
| 6,644,103 B1 | 11/2003 | Hall | |
| 6,659,976 B2 | 12/2003 | Beck et al. | |
| 6,662,650 B1 | 12/2003 | Durkee et al. | |
| 6,668,645 B1 | 12/2003 | Gilmour et al. | |
| 6,750,468 B2 | 6/2004 | Malmstrom et al. | |
| 6,758,084 B2 | 7/2004 | Hall | |
| 6,921,911 B2 | 7/2005 | Siepmann | |
| 7,070,575 B2 | 7/2006 | Beck et al. | |
| 7,109,512 B2 | 9/2006 | Wirthlin | |
| 7,109,513 B2 | 9/2006 | Merz | |
| 7,161,165 B2 | 1/2007 | Wirthlin | |
| 7,259,383 B2 | 8/2007 | Wirthlin | |
| 7,304,583 B2 | 12/2007 | Beller | |
| 7,339,657 B2 | 3/2008 | Coates | |
| 7,459,713 B2 | 12/2008 | Coates | |
| 7,508,312 B2 | 3/2009 | Chajec | |
| 7,535,571 B2 | 5/2009 | Dietz et al. | |
| 7,652,767 B2 | 1/2010 | Harsh et al. | |
| 7,726,174 B2 | 6/2010 | Riley et al. | |
| 7,786,457 B2 | 8/2010 | Gao | |
| 7,805,978 B2 | 10/2010 | Riley et al. | |
| 7,818,992 B2 | 10/2010 | Riley et al. | |
| 7,907,282 B2 | 3/2011 | Coates | |
| 7,956,341 B2 | 6/2011 | Gao | |
| 7,987,722 B2 | 8/2011 | Hills | |
| 8,225,639 B2 | 7/2012 | Riley et al. | |
| 8,228,489 B2 | 7/2012 | Suzuki et al. | |
| 8,303,613 B2 | 11/2012 | Crandall et al. | |
| 8,362,432 B2 | 1/2013 | Maiden | |
| 2003/0025909 A1 | 2/2003 | Hallstadius | |
| 2004/0201835 A1 | 10/2004 | Coates et al. | |
| 2004/0238746 A1 | 12/2004 | Dreyer et al. | |
| 2005/0036147 A1 | 2/2005 | Sterling et al. | |
| 2005/0069468 A1 | 3/2005 | Huber et al. | |
| 2005/0285608 A1 | 12/2005 | Sato et al. | |
| 2008/0023659 A1 | 1/2008 | Dietz et al. | |
| 2008/0098798 A1 | 5/2008 | Riley et al. | |
| 2009/0018416 A1 | 1/2009 | Walker et al. | |
| 2009/0073433 A1 | 3/2009 | Myrick et al. | |
| 2010/0208243 A1 | 8/2010 | Suzuki et al. | |
| 2010/0289654 A1 | 11/2010 | Hunter et al. | |
| 2012/0138824 A1 | 6/2012 | Wen et al. | |
| 2012/0291421 A1 | 11/2012 | Darr et al. | |

FOREIGN PATENT DOCUMENTS

| | | |
|---|---|---|
| FR | 2492974 | 4/1982 |
| FR | 2791131 A1 | 9/2000 |
| JP | 58215538 A | 12/1983 |
| JP | 62-228142 A | 7/1987 |
| JP | 03-060646 A | 3/1991 |
| JP | 2004309296 A | 11/2004 |
| JP | 2008-256663 | 10/2008 |
| WO | 03030621 A2 | 4/2003 |
| WO | 2006/079797 A2 | 8/2006 |
| WO | 2010030251 A2 | 3/2010 |
| WO | 2010109416 A1 | 9/2010 |

OTHER PUBLICATIONS

Supplementary European Search Report dated Oct. 8, 2014 for related EP Application No. 12796298.
Chinese Office Action dated Aug. 27, 2015 for related Chinese Application No. 201280029918.8.
Japanese Office Action issued in related Japanese patent application No. 2014-514857.

* cited by examiner

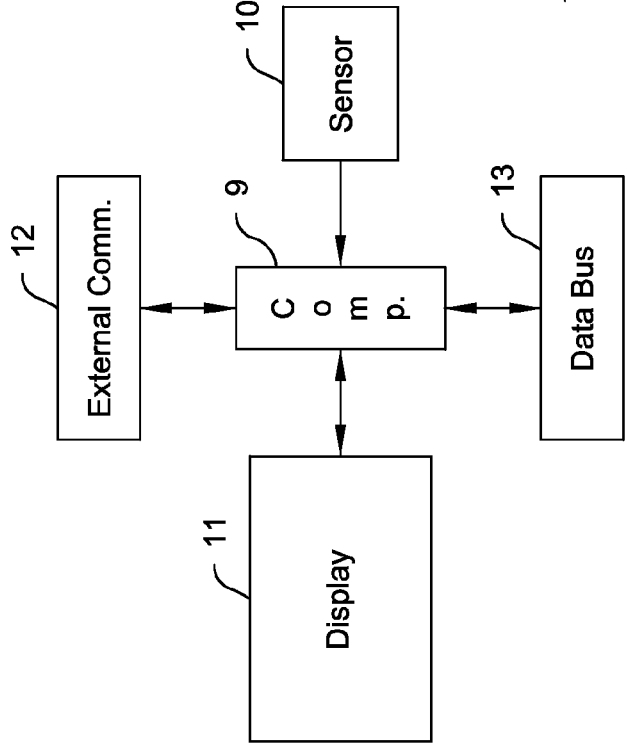
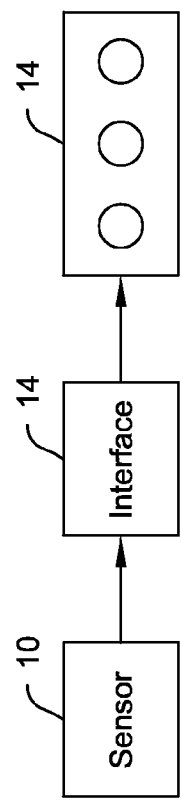

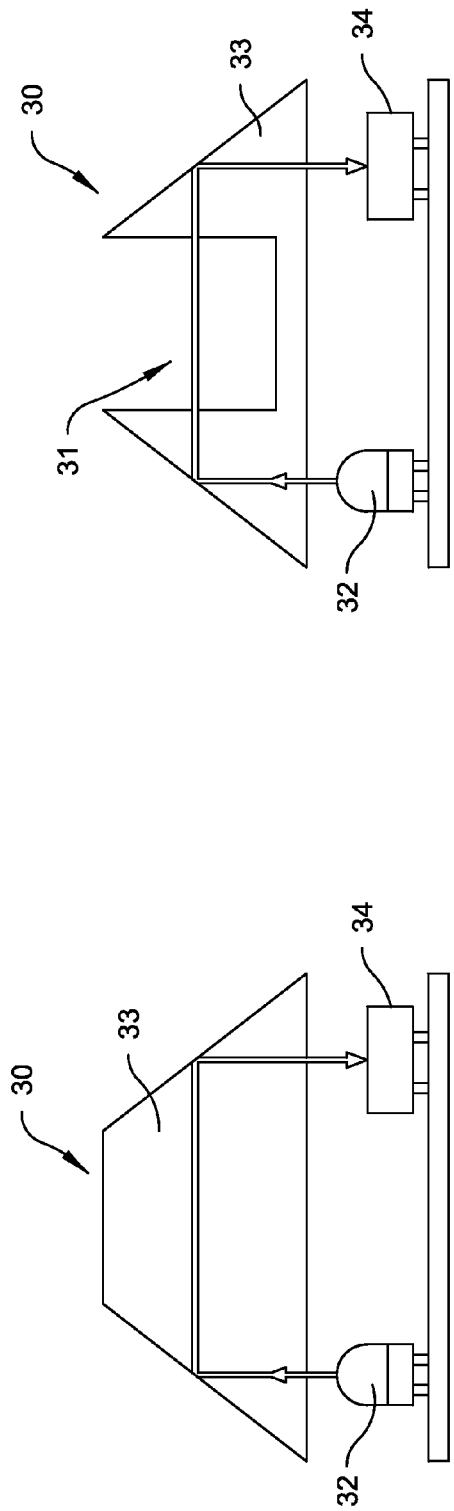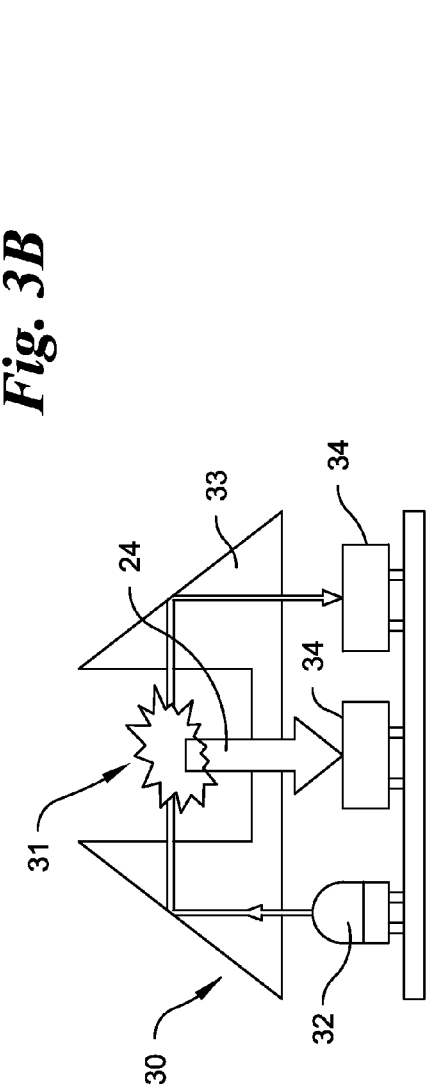
Fig. 3A   Fig. 3B   Fig. 3C

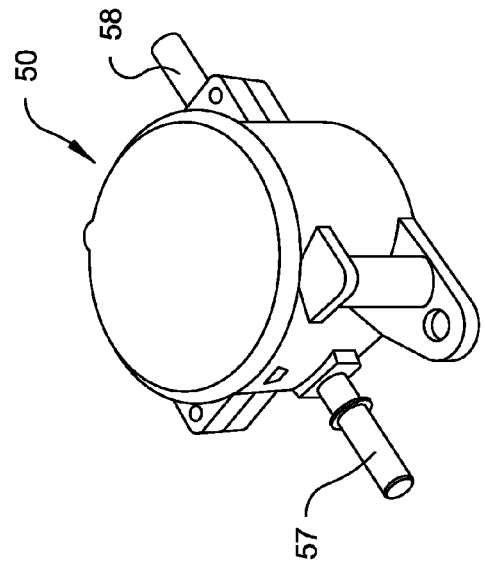
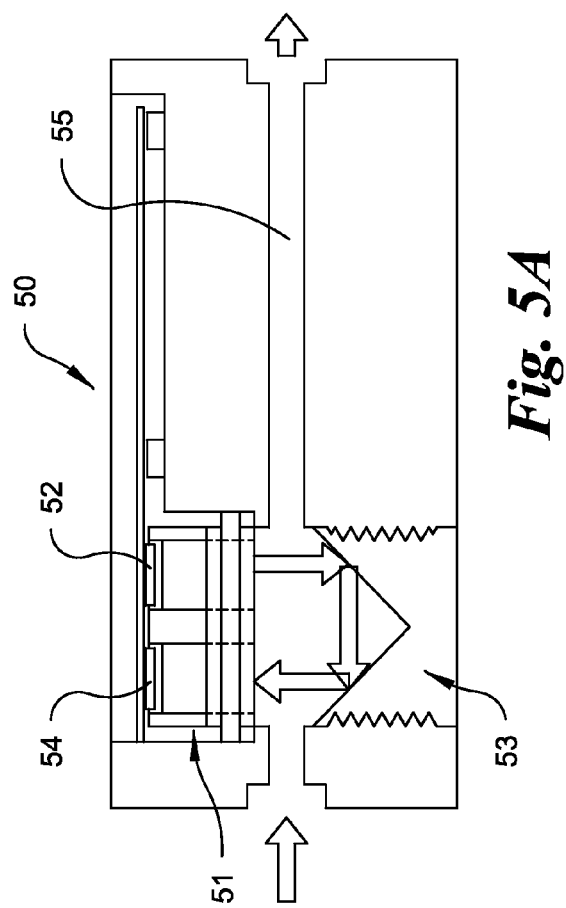
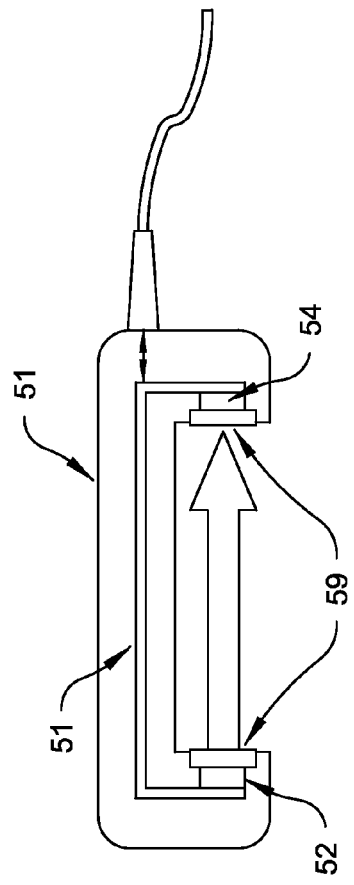
Fig. 5B
Fig. 5A
Fig. 5C

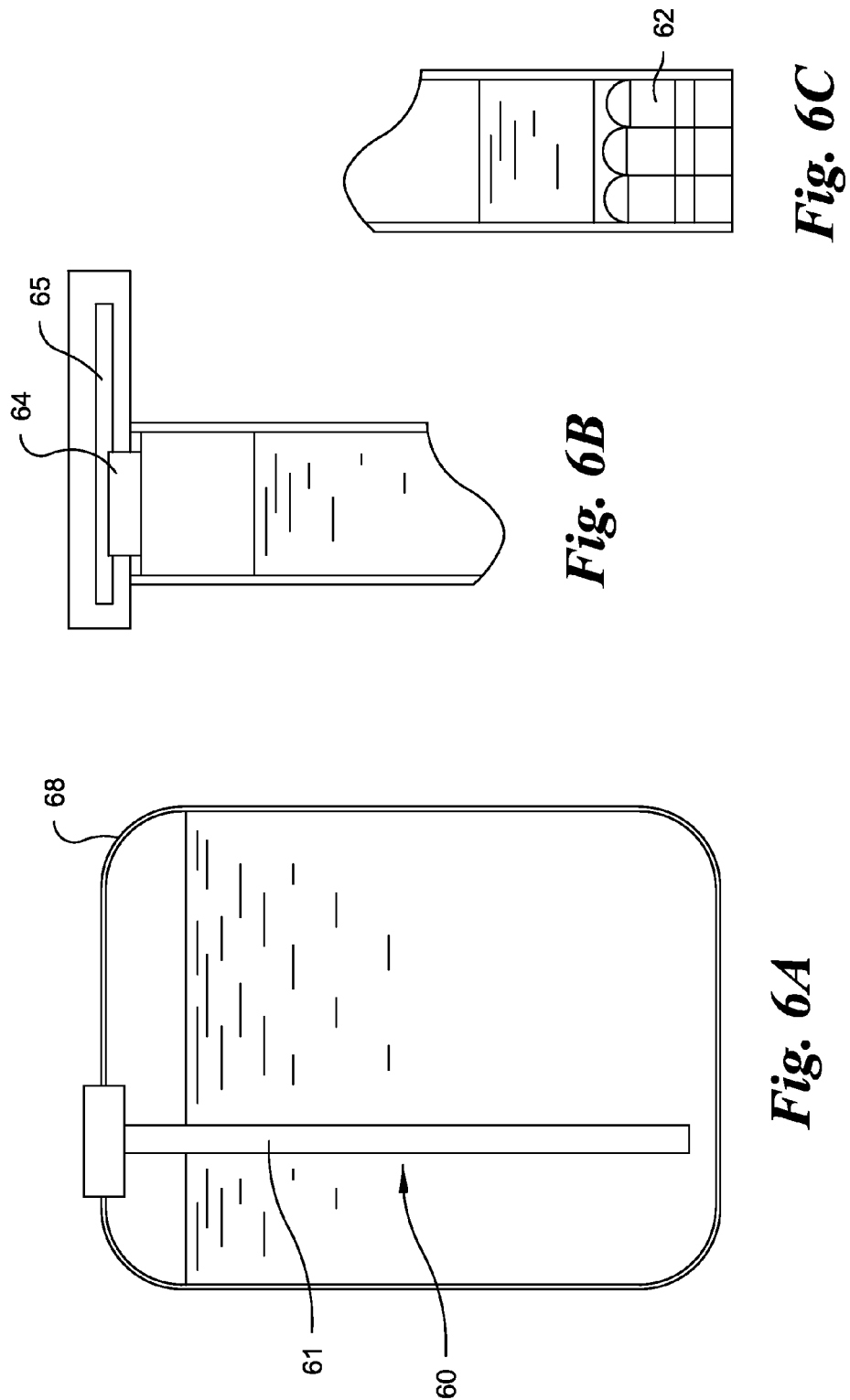

OPTICAL DEVICES FOR FLUID SENSING AND METHODS THEREFOR

CROSS-REFERENCE TO RELATED APPLICATIONS

This application is a divisional of co-pending U.S. patent application Ser. No. 14/124,601, which is a national stage application under 35 U.S.C. §371 of the International Application No. PCT/US2012/041431, entitled "OPTICAL SENSING DEVICE FOR FLUID SENSING AND METHODS THEREFOR," filed Jun. 7, 2012, and claims the benefit of U.S. Provisional Patent Application Ser. No. 61/520,308 entitled "LOW-COST IN-LINE AND IN-TANK FLUID QUALITY SENSORS BASED ON SPECTRAL MEASUREMENT PRINCIPLES" filed on Jun. 7, 2011, the subject matter of each of which is incorporated herein by reference, in its entirety, for all purposes.

FIELD OF THE INVENTION

The present disclosure relates to optical sensors and associated systems. More particularly, it relates to optical sensors and fluid monitoring systems used in, for example, the heavy equipment, automotive and transportation industries.

BACKGROUND

The role of optical spectral measurements for the monitoring of static and dynamic fluid systems is well established in the field of spectroscopy. Traditional systems may include the use of a spectrometric measurement system, such as a spectrometer or photometer, optically interfaced to a fluid stream, such as a liquid or gas. In the case of spectrometer systems, commercial dispersive near-infrared (NIR) or Fourier transform infrared (FTIR, near- and mid-IR) instruments often utilize various optical sensors used in transmission, transflectance (a combination of transmittance and reflectance) and internal reflectance modes of operation. U.S. Pat. No. 7,339,657, hereby incorporated by reference in its entirety, discusses each of these modes of operation as implemented into various optical sensor packages.

More generally, optical spectroscopy, for example, in the form of infrared spectroscopy is a recognized technique for the analysis and characterization of various types of fluids used in industrial, automotive and transportation applications, including lubricants, functional fluids and diesel emission fluids (DEF), which is marked under the ADBLUE® trademark of Verband der Automobilindustrie E.V. (VDA). Such spectroscopic measurements can provide meaningful data about the condition of the fluid and the fluid system during service. The term infrared spectroscopy is used in the broadest sense, and includes both near infrared and mid-infrared, and covers the region from 700 nanometers (nm) to 25,000 nm.

Infrared spectroscopy, as defined above, can provide measurement of fluid quality, such as DEF quality, and fluid properties, by way of example only, oxidation, coolant contamination, fuel dilution, soot, and content. In most cases, this information is derived directly as a measure of the chemical functionality, as defined by the characteristic vibrational group frequencies observed in the near infrared and infrared spectra. Further, the UV and visible spectra may provide information derived from color and/or information derived from electronic transitions and can be applied to provide information about oxidation, moisture and additive content, by way of example.

While the infrared spectral region is definitive in terms of the measurement of materials as chemical entities, the measurements can be difficult to implement in terms of the materials used. More specifically, the optics and associated materials used in these measuring devices are relatively expensive and do not always lend themselves to easy replication for mass production.

Moreover, when multiple devices are implemented into a larger monitoring system used in, for example, automotive monitoring applications, these systems often become prohibitively large, complex, and expensive. Another factor to consider is the operating environment. If a monitoring system is to be used in a relatively benign environment, such as in a laboratory under standard ambient conditions or in a climate conditioned indoor facility, then a device construction of the prior art may be used. However, if there is a requirement to measure a fluid system in a less conducive environment, such as on a process line (indoors or outdoors), on a vehicle, or a mobile or fixed piece of equipment, then it is necessary to consider a system more capable of operating under such conditions. This may include considering the temperature sensitivity of the components, as well as their robustness in terms of long-term exposure to continuous vibrations. Additional factors for consideration include size, thermal stability, vibration immunity and cost.

Alternative fluid measurement systems and techniques for fluid sensing and monitoring that address one or more of these considerations are desired.

SUMMARY

According to one embodiment of the present disclosure, an optical spectral sensing device for determining properties of a sample is provided. The device includes an elongated porous body having a first end and a second end. A solid-state emitter source is arranged at the first end of the body and a solid-state detector is arranged at the second end of the body. An electronics package is operatively connected to the device for providing energy to the solid-state emitter, and for receiving a signal generated by the detector. The body is configured to be at least partially submerged in the sample, and the electronics package is configured to determine a value of the depth of the fluid or of the depth of submersion of the body, and to output at least one value indicative of the depth of submersion of the body or depth of fluid.

A low-temperature safe sensor package is also provided. The package includes a housing defining an internal cavity therein for communicating with a fluid to be sampled. A sensor carrier is moveably arranged within the internal cavity and is biased into an operating position within the cavity by a spring element arranged between the sensor carrier and a portion of the housing.

A method for determining in a sample a concentration of a first fluid in a second fluid is also provided. The method comprises the steps of detecting a first intensity of radiation transmitted through the sample by a first beam having a first path length at a reference frequency ($f_{ref}$); detecting a second intensity of radiation transmitted through the sample by a second beam having the first path length at a frequency corresponding to an absorption peak of the first fluid; detecting a third intensity of radiation transmitted through the sample by a third beam having a second path length at the reference frequency; and detecting a fourth intensity of radiation transmitted through the sample by a fourth beam having the second path length at a frequency corresponding to an absorption peak of the second fluid. The temperature of the sample is then determined. A value equal to (the second intensity/the first intensity)−(the fourth intensity/the third intensity) is then calculated. Finally, a value of the concentration of the first fluid and the second fluid is calculated based on the value of (the second intensity/the first intensity)−(the fourth intensity/the third intensity), the detected temperature, and stored calibration data.

BRIEF DESCRIPTION OF THE DRAWINGS

FIGS. 2A and 2B are schematic diagrams illustrating exemplary methods of integrating monitoring systems according to embodiments of the present disclosure into a vehicle or heavy equipment application.

FIGS. 3A-3C are cross-sectional views of various optical packages which may be used by sensors according to embodiments of the present disclosure.

FIGS. 5A-5C illustrate embodiments of in-line (FIGS. 5A and 5B) and submersible (FIG. 5C) sensors according to embodiments of the present disclosure.

FIGS. 6A-6C illustrate an exemplary in-tank sensor for measuring both fluid level and composition according to an embodiment of the present disclosure.

DETAILED DESCRIPTION

Figure 1C:
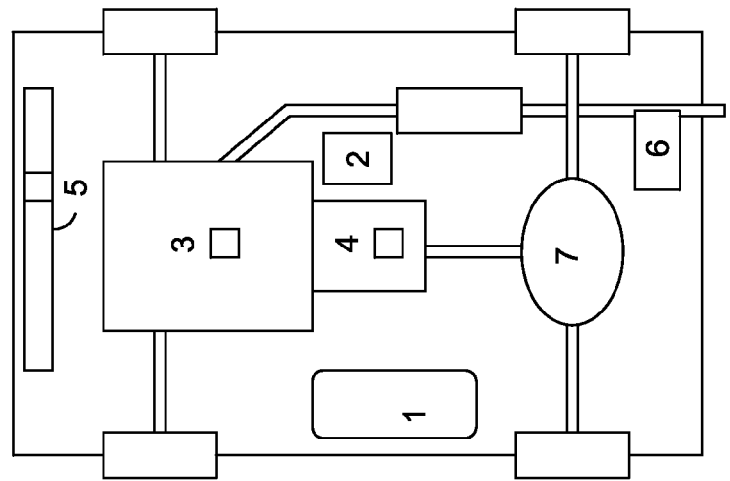
FIGS. 1A-1C are schematic diagrams illustrating an exemplary fluid monitoring system as implemented into a vehicle or heavy equipment application.

It is to be understood that the figures and descriptions of the present invention have been simplified to illustrate elements that are relevant for a clear understanding of the present invention, while eliminating, for purposes of clarity, many other elements found in fluid measuring systems, including those utilizing spectroscopy. However, because such elements are well known in the art, and because they do not facilitate a better understanding of the present invention, a discussion of such elements is not provided herein. The disclosure herein is directed to all such variations and modifications known to those skilled in the art.

In the following detailed description, reference is made to the accompanying drawings that show, by way of illustration, specific embodiments in which the invention may be practiced. It is to be understood that the various embodiments of the invention, although different, are not necessarily mutually exclusive. Furthermore, a particular feature, structure, or characteristic described herein in connection with one embodiment may be implemented within other embodiments without departing from the scope of the invention. In addition, it is to be understood that the location or arrangement of individual elements within each disclosed embodiment may be modified without departing from the scope of the invention. The following detailed description is, therefore, not to be taken in a limiting sense, and the scope of the present invention is defined only by the appended claims, appropriately interpreted, along with the full range of equivalents to which the claims are entitled. In the drawings, like numerals refer to the same or similar functionality throughout several views.

The term "processor" when used herein generally refers to a circuit arrangement that may be contained on one or more silicon chips, and/or integrated circuit (IC) boards, and that contains at least one Central Processing Unit (CPU), and may contain multiple CPU's. The CPU may generally include an arithmetic logic unit (ALU), which performs arithmetic and logical operations, and a control unit, which extracts instructions from memory and decodes and executes them, calling on the ALU when necessary.

Processors may take the form of a microprocessor, and may be a low power CMOS processor with an embedded analog to digital converter, by way of non-limiting example only. The present invention is operable with computer storage products or computer readable media that contain program code for performing the various computer-implemented operations. The non-transitory computer-readable medium is any data storage device that can store data which can thereafter be read or accessed by a computer system component such as a microprocessor. The media and program code may be those specially designed and constructed for the purposes of the present invention, or they may be of the kind well known to those of ordinary skill in the computer software arts. Examples of computer-readable media include, but are not limited to magnetic media such as hard disks, floppy disks, and magnetic tape; optical media such as CD-ROM disks; magneto-optical media; and specially configured hardware devices such as application-specific integrated circuits (ASICs), programmable logic devices (PLDs), and ROM and RAM devices. Examples of program code include both machine code, as produced, for example, by a compiler, or files containing higher-level code that may be executed using an interpreter.

The term "electronics package" as used herein is to be understood broadly and includes any configuration of electronic components for use in providing power to components, such as LED's and detectors, control signals to such components, receiving data from such components, performing calculations and signal processing on data received from such components, storing received and processed data, and providing outputs of such data to monitoring and display systems. Such packages may include discrete analog and digital components, batteries, integrated circuits configured to include multiple analog and/or digital logic components, general purpose and special purpose processors, data storage devices of all descriptions including magnetic, capacitive, random access, read-only and other non-transitory storage media, wireless and wired transmitters, receivers, and transceivers, and other devices, in discrete and integrated form.

The detectors and emitters of all embodiments disclosed herein may be integrated into and integrally formed with electronic packages, such as on printed circuit boards such as control boards of such packages. Alternatively, the detectors and emitters may be configured to be mounted separately from control boards and other electronic devices Fluid measuring/monitoring systems according to embodiments of the present disclosure take into account factors of size, thermal stability, vibration immunity and cost, and are configured to facilitate mass production. Sensors and monitoring systems according to embodiments of the present disclosure may simplify the complex arrangements of the prior art by providing a wavelength specific light or energy source (or sources), a device for interfacing with the sample, and one or more detectors. These simplified spectrometric/photometric systems can be made relatively small and compact compared to the large and expensive monitoring systems of the prior art, while retaining their functionality and reliability in harsh environments.

These systems may include the use of solid-state light emitters (e.g. LEDs), low-cost, solid state detectors, integrated with opto-electronics that reduce temperature dependency effects, low-cost optics that may be mass-produced such as by molding techniques (if required), and low-cost packaging. Residual temperature effects may be handled by thermal modeling and the application of compensation algorithms.

The sensor devices described in this disclosure may be implemented as monitoring devices for water-based fluids, such as DEF and coolants, in addition to fuels, lubricants and other functional fluids used in automotive vehicles, heavy equipment, and various forms of transportation that involve dynamic fluid lubricant and power conversion systems. They may include sensor devices for monitoring engine oils, transmission oils, hydraulic oils and fluids, turbine oils, coolants and any fluid system that protects mechanical moving parts or transmits power to moving parts. Throughout the disclosure, the term fluid is considered in the broadest sense, and can include gases and vapors, which include off-gassing vapors from fuels, slip and bypass gases from combustion zones, and exhaust gases. In one or more configurations, the sensor can be operated immersed in the fluid, and measurements can be made in a static environment such as a tank or storage vessel, or in a moving environment, such as a fuel line or exhaust pipe. It is understood that the period of measurement may vary from less than a second, to a few seconds, to periods of days or longer, such as for systems where the change in fluid composition (chemistry) changes slowly, if at all. When used for fluid quality assessment the sensor is intended to monitor for changes in composition, including contamination from the use of an incorrect fluid.

Figure 1A:
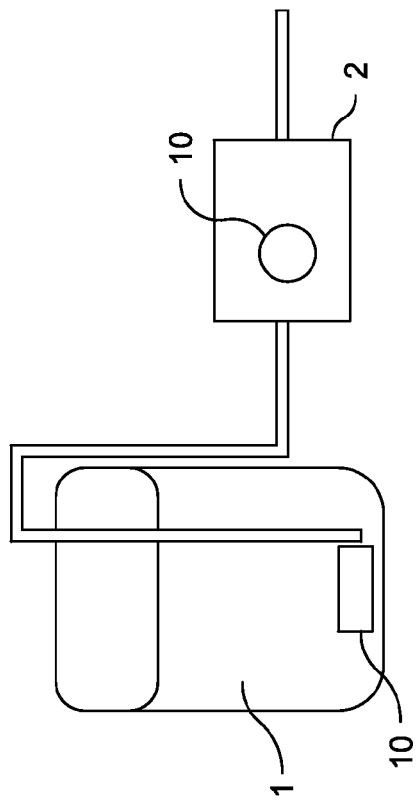
Figure 1B:
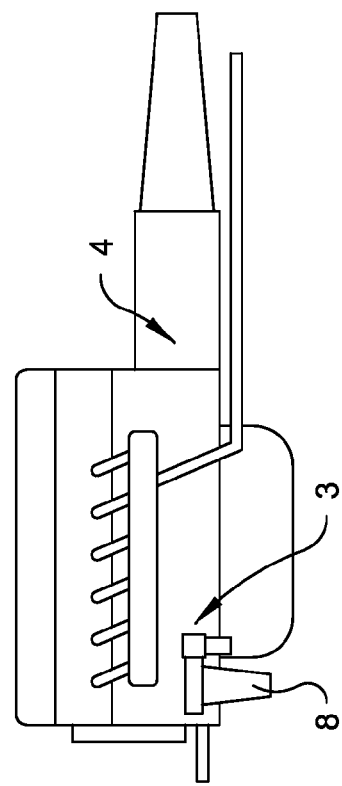

Referring generally to FIGS. 1A-1C an exemplary fluid monitoring system is shown as implemented into an automotive or heavy equipment application. As set forth above, sensors according to embodiments of the present disclosure may be suitable for fluid monitoring in all aspects of equipment operation. With reference to FIGS. 1A and 1C, for applications such as DEF quality monitoring, a sensor 10 may be located within a given fluid stream, such as in the feed lines or in a fluid dosing system 2. Further, a sensor may be configured as a submersible component located within a feed tank 1 (e.g. a DEF or fuel tank).

Referring generally to FIGS. 1B and 1C, sensors according to embodiments of the disclosure may also be used for oil condition monitoring (e.g. oxidation and nitration) in gasoline and natural fired engines. For this application, sensing devices may be located at the output side of an engine's 3 primary (or secondary) filtration system, where a filter 8 is inserted into the stream on the return side of the filter-housing block. Advantages of mounting the sensor on the filter block include convenient access, external mounting, and reduced operating temperature. Alternative positions for the sensors described herein may include the transmission 4, the coolant system 5 and the rear axle 7. Another sensor position is within a relatively cooler location of the exhaust system 6, wherein a heat-insulated probe and sensor can monitor exhaust gas for species such as NOx (see also FIG. 4B). While many of the embodiments of the present disclosure are described in the context of sensor devices installed on a vehicle, or a combustion engine powered system, this serves only as appropriate examples. The devices are, as indicated, intended for use in all forms of fluid measurement systems.

With reference to FIGS. 2A and 2B, with one or more sensors on board a vehicle or piece of equipment, the measured data may be provided to a display or on-board data handling system. Embodiments of the present disclosure may communicate sensory output back to the operator/driver via one or more alarms, alerts, displays or status lights. Referring to FIG. 2A, in one implementation, a standalone system 20 includes a functional display and associated interface hardware 14 directly responsive to the output of a sensor 10 for communicating data to an operator. This type of interface may be advantageously implemented as a retrofit to an existing vehicle or piece of equipment. With reference to FIG. 2B, in other embodiments, however, the measurement systems may be more fully incorporated into the vehicle's original equipment (OE) control/computer systems. For example, the output of one or more sensors 10 may be provided to the vehicle's management system, including an on-board computer or data management processor 9. From this management system, sensory output data may be provided to, for example, an operator display 11, an external communication device 12 (e.g. a transmitter for communicating with a remote monitoring system), or stored into memory via a data bus 13 for further processing or retrieval. It should be appreciated that sensors 10 may receive power provided by data bus 13 or through the normal power distribution system of the vehicle.

Sensors according to embodiments of the present invention generally comprise low-power consumption devices internally operating at 3.5 to 5 volts, and configured to receive and process input voltages normally found on vehicles and ranging from 12 to 40 volts DC. The sensors can be configured with various electronics packages, such as a simple digital output device or a smart sensor that provides processed numerical data. The output from the sensor can be provided directly to any suitable type of display, such as a simple status light, for example, a three state LED: green (OK), yellow (warning) and red (alert or problem), or to an alpha-numeric or a graphical display, for example, an LCD display. Alternatively, the sensor can provide a standardized format output (e.g. SAE J1939) to the vehicle or equipment data bus 13, such as the CAN bus (e.g. a 5V-Highspeed-CAN, 250 kbit, ISO11898) of a vehicle, supplying diagnostic data (OBDI/II) either to an on-board computer, which in turn supports and intelligent sensor output display 11.

Sensors described herein may utilize any suitable optical package, operating in a variety of modes (e.g. internal reflectance or transflectance formats), as set forth in U.S. Pat. No. 7,339,657. For example, with reference to FIG. 3A, sensors according to embodiments of the present invention may comprise a light source 32, a reflector 33 and detector 34 configured for an internal reflectance mode of operation. Likewise, transmittance mode (FIG. 3B) and light scattering 24 (FIG. 3C) modes may be implemented. These embodiments may include the formation of an open path or channel 31 in reflector 33 to allow fluid to flow between a pair of opposing optical surfaces, thus providing a transmission path for the optical beam. In the transmittance mode, the absorption measurement is proportional to the thickness of the channel 31. Accordingly, this channel may be formed as, for example, a narrow slot for opaque or highly absorbing fluids, or as a wider cavity or channel for lower absorption samples.

It should be noted that in the transmission mode (FIG. 3B), multiple LED source components may be configured in close proximity or co-packaged with a near-common light path. The system can utilize a comparable set of detectors (or a reduced detector set) dependent on the final beam path and divergence through the optical structure (not illustrated). This is an important facet and is utilized in the fluid quality monitors for enabling multi-component monitoring. For example, a DEF quality monitoring system may be provided that utilizes LEDs (and corresponding detectors) at a reference wavelength, and wavelengths corresponding to absorption peaks of two or more fluids in a two or more fluid sample, such as three LEDs at wavelengths of 810 nm (reference), 970 nm (which corresponds to absorption peaks in water and hydroxyl), and 1050 nm (which corresponds to an absorption peak in urea).

Figure 4A:
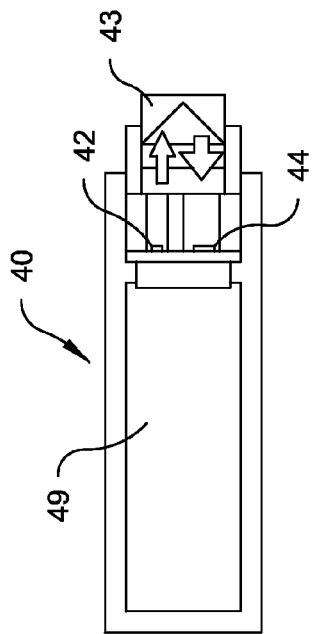
FIGS. 4A and 4B are cross-sectional views of insertion style sensors according to embodiments of the present disclosure.
Figure 4B:
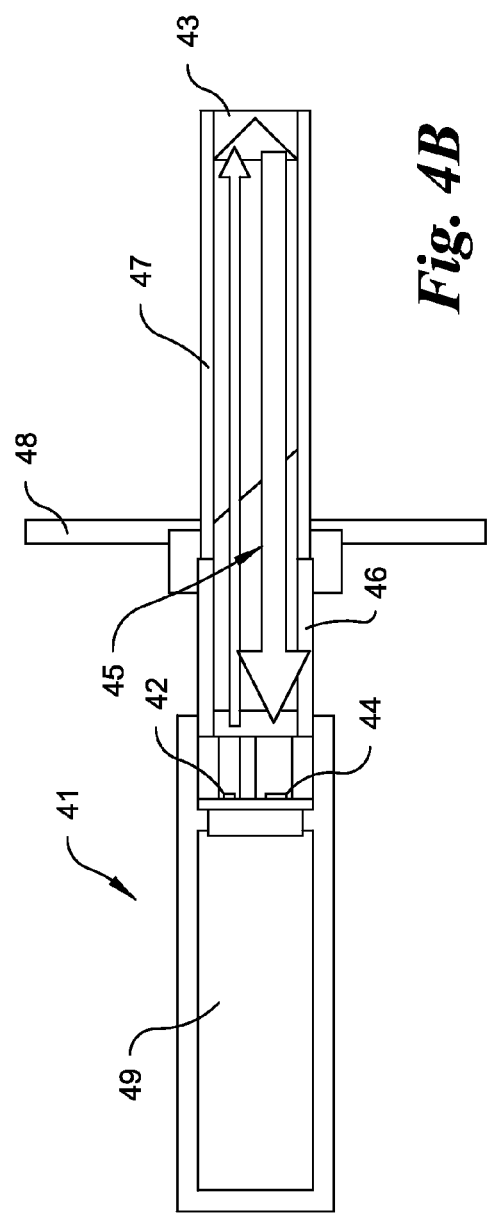

Referring generally to FIGS. 4A and 4B, embodiments of the present disclosure include insertion-style sensors used for measuring one or more properties of liquids (sensor 40, FIG. 4A) and gases/vapors (sensor 41, FIG. 4B). Sensors 40,41 are shown utilizing an internal reflectance configuration. Each sensor 40,41 comprises an electronics package 49 for controlling the sensor's opto-electronics including LED(s) 42 and detector(s) 44 in combination with a reflector 43 (e.g. a slotted reflector). Note that the number of detectors used is a function of the illumination area (from the source), the desired sensitivity (as defined by the signal-to-noise ratio, SNR) and the available space. In the illustrated embodiment, sensor 40 may be used in a liquid insertion environment configured for longer path lengths. In this layout reflector 43 is located at a distance that provides the desired net path length, while taking into account the total path traversed by the retro-reflected radiation. Sensor 41 comprises an extended path length 45 and is intended for gas and vapor measurements. Other embodiments may include an optional protective heat barrier 46 intended for exhaust gas or other high-temperature applications (e.g. through exhaust pipe 48). The introduction of the gases into sensor 41 is passive and relies on permeation of the gases/vapors through a medium such as a stainless steel gauze or membrane 47.

Referring generally to FIGS. 5A-5C, sensors according to embodiments of the present disclosure also include in-line and submersible packages. For example, FIG. 5A is a cross-sectional view illustrating an in-line (flow-through) sensor 50 with an adjustable retro-reflective insert 53, and an electronics package 51 including at least one light source 52 and at least one detector 54. This interchangeable insert 53 may be used for fine adjustment of the optical path length, or reflector type, without the need to replace the entire sensor package. As illustrated, energy from light source 52, typically a multi-wavelength device, passes through the fluid in chamber 55 and back to detector 54 along the path shown in FIG. 5A. The transmitted energy (typically UV-visible-NIR) interacts with the sample fluid, with the characteristic absorptions of the fluid modifying the light transmission of the fluid, and is subsequently sensed by detector 54. The selectivity of the absorption is defined by the wavelengths of the source(s), which may also be effected by the combination with the optical filters integrated with the detectors. FIG. 5B shows an exemplary perspective view of sensor 50 of FIG. 5A, including connectors 57,58 in communication with chamber 55 for interfacing with a fluid feed path (e.g. a fuel line).

In an alternative embodiment illustrated in FIG. 5C, sensor 51 operates in a "staring" mode, wherein electronics package 51 includes a light source 52 (e.g. LED) and a detector 54 located generally opposite one another, between which is arranged a sensing area 59. While sensor 51 may be intended to be used as a submersible sensor that can be located within, for example, a fluid dosing tank, this configuration is not constrained to in-tank usage, and can be integrated into a flow-through system.

Figure 14:
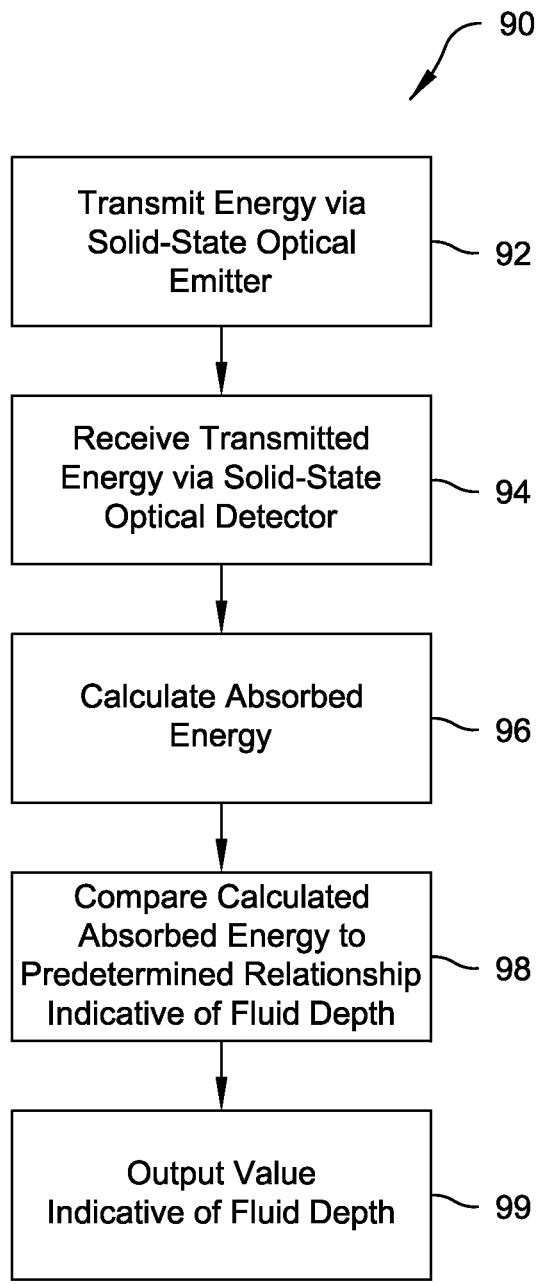
FIG. 14 is a process diagram illustrating a method of determining the depth of a fluid according to the embodiment of FIGS. 6A-6C.

The geometries shown for the sensors illustrated in the previous FIGS. 4A and 5A-5C are based on the absorption profiles for the common fluids in the NIR to mid-IR spectral regions providing path lengths from a few millimeters to about 50 mm. The gas measurement path length for the gas implementation shown in FIG. 4B can be longer, and with the folded geometry a path length of up to 500 mm can be considered. However, an alternative in-tank embodiment of the present disclosure for measuring both fluid level and fluid quality/composition in an in-tank application is illustrated in FIGS. 6A-6C. In this staring mode embodiment, the path length is defined by the volume of fluid in a tank 68 and the anticipated depth of fluid. In this embodiment, the depth to be measured may be of a liquid, and not of a gas, the volume above the level of the liquid being of gases. More specifically, sensor 60 is housed in an elongated porous body or housing 61, which may be in the form of a hollow tube, which may be cylindrical. The active components (e.g. a light source/LED(s)) 62 of the sensor may be mounted at the lower end of housing 61 (FIG. 6C). The receiver or detector 64 may be arranged on an opposite end (FIG. 6B), for example, at the top of tank 68 with the associated control and data processing electronics 65. The light source 62 and detector 64 may be so arranged and oriented that the light source 62 transmits radiation along body from one end to another, and may further in an embodiment transmit radiation through the hollow interior of the body 61 to detector 64. The mounting of the light source 62 within the hollow body may tend to protect light source 62 against physical shock. Wiring to transmit power and control signals to light source 62 may be within the hollow body 61; in embodiments, light source 62 may be packaged in a sealed unit including one or more batteries or other internal source(s) of energy. In this embodiment, the absolute absorption measured may be correlated initially to path length or depth of fluid, and the relative absorptions of the fluid components are determined and correlated to the ratio(s) of the main components. More specifically, referring generally to FIG. 14, sensor 60 of FIGS. 6A-6C may be used in a measuring process 90 for determining the depth of a volume of fluid. In one embodiment, a light source (e.g. LED 62) is operative to transmit light energy through a volume of fluid (step 92). This energy is subsequently detected in step 94 a detector (e.g. detector 64). In step 96, a comparison is made between the magnitude of energy transmitted by LED 62 and the magnitude of the energy received by detector 64 to calculate energy absorbed by the fluid. Finally, in step 98, this absorption value is compared to a predetermined absorption vs. depth relationship, which may be stored in a memory device incorporated in electronics 65, for estimating or determining the depth of the fluid. This estimated or determined depth value may be output to, for example, a display device in step 99. As will be understood by one of ordinary skill in the art, these calculations may be performed by processing components incorporated into the control electronics (e.g. electronics 65).

Each of the above-described embodiments of sensors that form the basis of a solid-state measurement system utilize a spectrally selective source (e.g. an LED) and a detector. Embodiments described herein may utilize optical interfacing based on, for example, direct line of sight coupling of the source(s) and detector(s) (i.e. staring mode), or by a transflectance configuration, as set forth in greater detail in U.S. Pat. No. 7,339,657.

In one embodiment, the detectors comprise one or more silicon-based detectors. Silicon photodiode detectors have the advantages of high sensitivity over a broad spectral region (nominally 350 nm to 1100 nm), linearity, robustness, availability of a large number of packaging options, and low cost. Other solid-state light detectors may be implemented without departing from the scope of the present disclosure, such as InGaAs, PbS/PbSe and MEMS components.

Regarding the light sources, LEDs offer the advantages of color or wavelength specificity, constant output, low power consumption, no significant thermal output, output frequency modulation ability, compactness and robustness, availability in a large number of packaging options, and extremely low cost. A relatively wide range of spectral wavelengths are commercially available off the shelf for LED sources from 240 nm (far UV) to 3000 nm (mid-IR). Longer wavelengths are also available. Likewise solid-state detectors can be combined with optical filters to provide for wavelength selection. This integration can be a physical combination of a filter element with the detector device, or the filter may be processed onto the detector device at the wafer level.

Moreover, certain LEDs are commercially available with matching detectors, examples being the short-wave NIR LEDs, which are commonly used for remote "infrared" monitoring and control. Certain LEDs can operate at two or more states producing more than one wavelength (such as red, yellow and green) from a single device. This enables a very compact design using a single source and single detector, and where the output for individual wavelengths is differentiated by different modulation frequencies. In certain measurement systems up to four or five or more unique wavelengths (for example: blue, green, yellow, red and NIR wavelengths) will be monitored, each as individual wavelengths, each detected by a single (or multiple) detector, and differentiated based on modulation frequency. The multiple channels will be modeled to provide color profiling and multiple component determinations. LED packages including multiple LEDs may be used in the implementation of this configuration of the opto-electronics.

Embodiments of the present disclosure may also implement one or more integrated circuits for performing optical data processing, optical compensation, temperature compensation, analog and digital signal processing, and external communications. By way of non-limiting example only, embodiments of the sensors described herein may be comprised of one or more independently modulated LEDs coupled to an optical feedback system for monitoring the outputs of the LEDs, independent of the sampling channel. This system may include compensation for drift in the output of the LEDs as a function of temperature. The feedback detector may be located in close proximity to the system detector (e.g. after the optical interface) to model the response changes of the detector system. In an alternative implementation of the LEDs, a reference wavelength is used as a baseline reference point. Such a reference is located at a wavelength that does not absorb or interact with the fluid. An example implementation is used for DEF measurements, wherein an 810 nm LED is used as a reference wavelength. This secondary wavelength provides a reference independent of sample absorption, and as such can provide a direct ratio $I_0/I$ which is used to calculate the effective absorption (proportional to species concentration): absorption=$-\log(I_0/I)$, where $I_0$ is the reference intensity, and $I$ is the intensity after the sample absorption. The optical and electronics system can be a single integrated circuit board or device, possibly featuring (but not explicitly) application specific integrated circuits (ASICs) for the signal handling, computations and data communications. This integrated optoelectronic component may be encapsulated, and may include some imaging optics, accomplished for example by some form of molded optics in front of the source(s) and detector(s).

The placement of the opto-electronic elements (i.e. the LEDs and detectors) is important to ensure optimum imaging through the optical interfacing structure. In a standard environment, with moderate operating temperatures, the opto-electronics is close-coupled to the optical interfacing structure. Typical distances are expected to be from about 1 mm to 1 meter (1 m) or more. At the shorter distances, no additional imaging optics are contemplated. However, at longer distances, supplemental lenses made from glass or plastic may be placed in front of the LED source(s) and detector(s) to improve image quality. Alternatives will include the use of light conduit, from the optical interfacing structure to the opto-electronics. Light conduits can be in the form of glass or plastic rods (index matched or otherwise) or optical fibers.

Packaging of the embodiments of the present disclosure may include fabricating housings from low-cost materials. Examples can include aluminum moldings or extrusions, machined plastics, plastic moldings and extrusions, and porous metallic mesh, as in the case of submersible sensors (FIGS. 5A-6C). Fluids such as DEF may be aggressive to materials such as aluminum, and metals such as stainless steel. Components of sensor packages may be made of plastics such as polyolefins, polysulfones and polyethers (such as DELRIN(R) brand acetal resin of E.I. DuPont de Nemours and Company), by way of example, to prevent corrosion or damage from the fluid. The selection of material will be based on the requirements of the application and cost. In cases where high temperature applications are involved (80° C. or higher), a provision for providing external cooling fins and the use of thermally insulating materials between the optical structure and the opto-electronics are provided as options in the design.

As set forth above, sensor packages must be able to reliably perform in harsh environmental conditions. For example, fluid sensors in an automotive application encounter temperatures from −40° C. to 80° C. for external installations, and −40° C. to 130° C. for under the hood applications (for engines) for fluid flow, and up to 200° C. for instantaneous storage temperatures. Sensors have recommended operational temperature ranges for specific applications. A primary specification is that the sensor can survive the temperature range without sustaining physical, mechanical or electronic damage. A further temperature specification is a range for actual operation. This is typically tied to the working temperature range of the fluid. A practical example is DEF, wherein the fluid freezes below −11° C., and can degrade at temperatures above 60° C.

Freezing of aqueous based systems is especially problematic where there is a captive area wherein fluid exists or flows (e.g. in a closed system). For example, water can expand up to 10% in volume as it freezes. Certain fluids, such as certain DEFs, also expand in volume upon freezing. Thus, it is important to provide a method that accommodates this expansion. Without consideration, the structure holding the fluid, or the sensors included therewith, can be mechanically stressed, and can break or fracture.

Figure 7A:
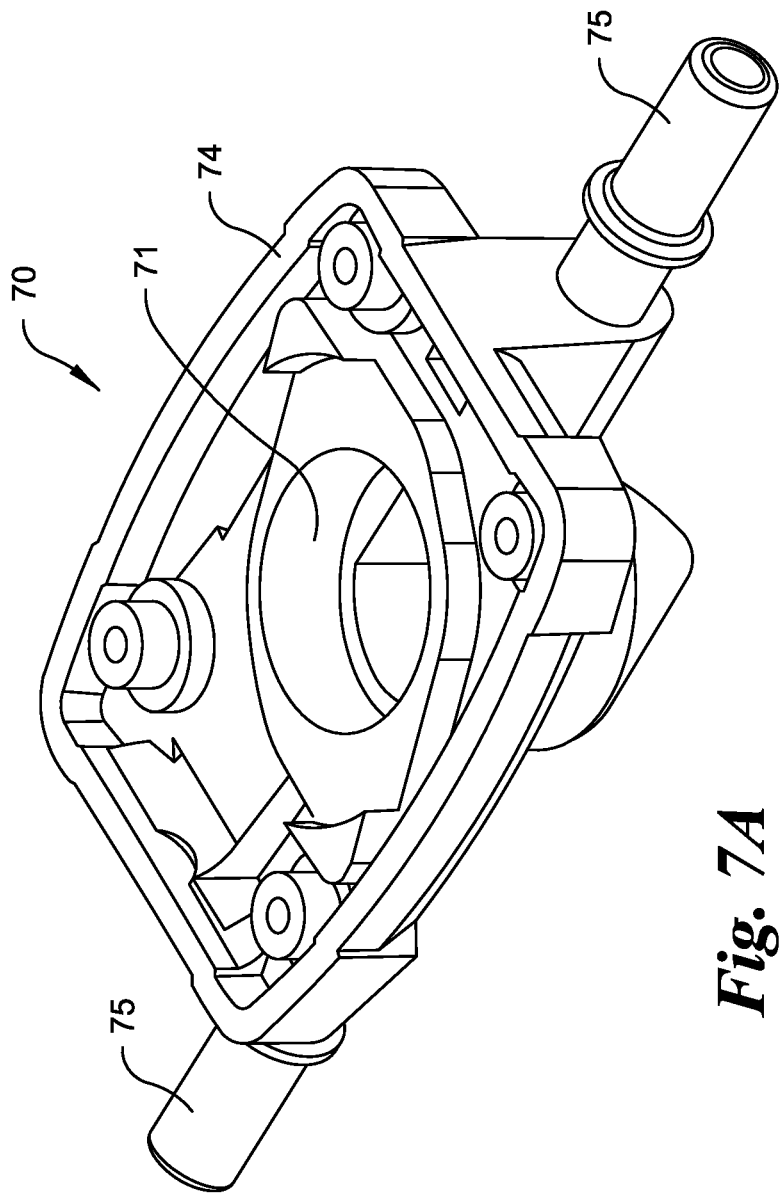
FIGS. 7A-7C are partial, exploded, and assembled perspective views, respectively, of an exemplary sensor and housing configured to protect against hard frost conditions.
Figure 7B:
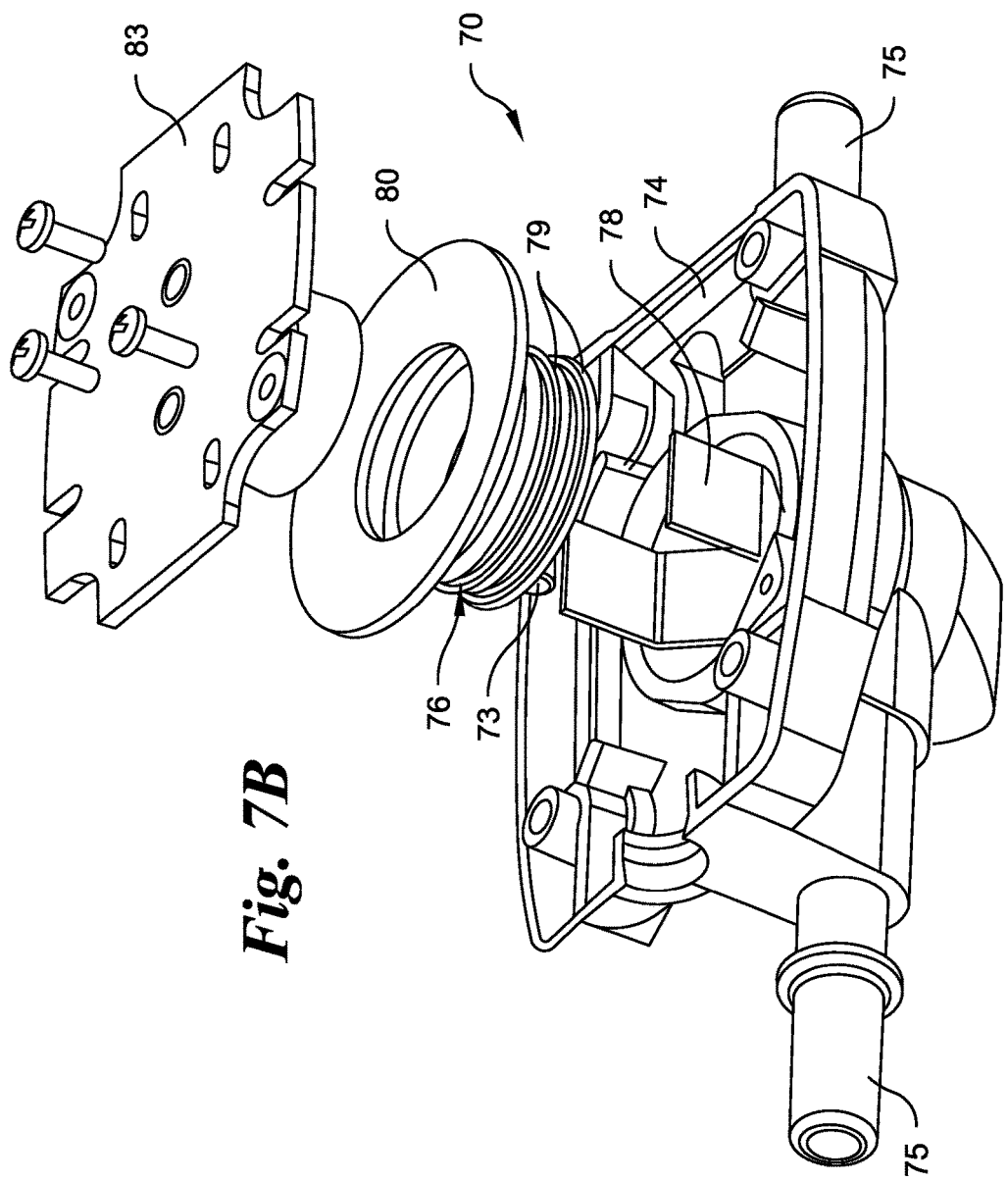
Figure 7C:
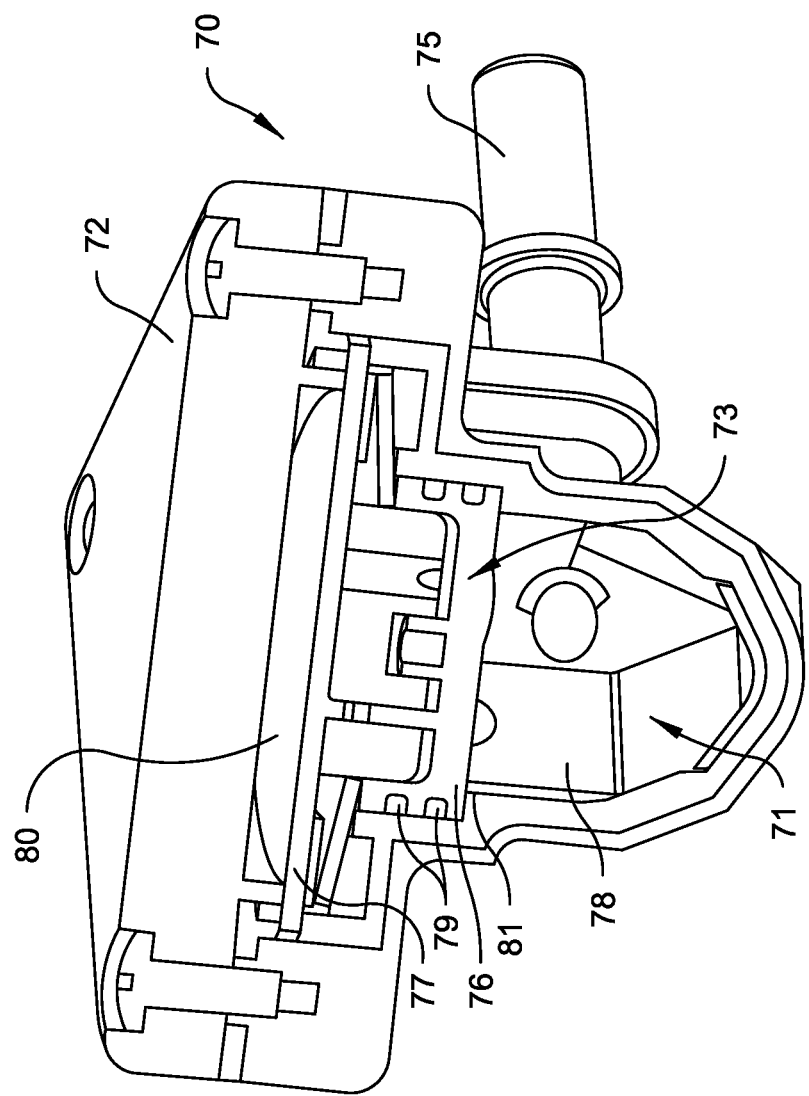

Referring generally to FIGS. 7A-7C, embodiments of the present disclosure incorporate a configuration of an optical sensor package, such as an in-line fluid property sensor, that provides hard frost protection and prevents or mitigates physical damage upon the freezing of a fluid contained therein. These embodiments include a mechanism that behaves as a piston working against the counter pressure of a high tension spring. More specifically, an embodiment of a sensor 70 may include a housing, such as a two-part housing including a lower portion 74 having ports 75 (e.g. an inlet and an outlet) arranged thereon, and an upper part 72 (FIG. 7C). Lower portion 74 of the housing defines an internal cavity 71 in communication with ports 75 for providing a fluid to be sampled thereto. A piston-like sensor carrier 76 is moveably arranged within internal cavity 71. The carrier 76 may be elastically mounted in cavity 71, such as by flexible biasing fingers joining carrier 76 to an inner wall of cavity 71, thereby both biasing and retaining carrier 76. A spring element 80, which may be a Belleville washer, is arranged between a portion of the housing and sensor carrier 76. An optical package 73 is arranged on and carried by sensor carrier 76. Sensor carrier 76 is sealed to an internal wall of lower portion 74 by sealing element 79, which may be a double o-ring seal, rendering cavity 71 a closed cavity for fluid transmission via ports 75. As a fluid within cavity 71 expands with freezing, if the frozen material engages and applies force in excess to the holding force of the spring element 80 to optical package 73 and/or carrier 76, carrier 76 is displaced generally upwards against the biasing force of spring element 80. This displacement relieves the stresses that might otherwise cause breakage or damage to either the housing or the optical package. As the frozen fluid melts with increased temperature, optical package 73 is urged back to its operating position against a fixed mechanical stop 81 defined in the housing via pressure exerted by the spring element. This spring bias and fixed stop 81 arrangement ensures that path length and optical alignment integrity is retained, or re-realized, when carrier 76 is returned to the operating position despite the movement of the optical package during freezing conditions. The spring element 80 may be selected such that the carrier 76 is not displaced under normal fluid operating pressures. A circuit board 83 may be provided, including control circuits, for operating the sensor's optical package.

When used in a flow mode application, below the freezing point, solid material is generally retained within sensor packages. Even as these systems thaw with increased temperature, the short-term retention of solid material can nonetheless constrict the flow of fluid through the sensor. In order that the sensor not constrict the system, there may be a requirement to thaw the sensor, or to prevent the fluid contained therein from freezing, to enable system operation. This may be provided via an embedded heating element 78 arranged within sensor housing 72,74. Heating element 78 may comprise a physical element (e.g. an electrically conductive polymer or other material having electrically resistive properties) provided, for example, around an exterior portion of cavity 71, or may be integrated into sensor housing 72,74. In such an embodiment, circuit board 83 may further be configured with a temperature detector, and to provide electrical power to heating element 78 in response to detecting a temperature at or below the freezing point of the fluid. Circuit board 83 may further be configured to detect frozen material via processing optical signals. In another embodiment, the heating component is arranged externally to an outer wall of the sensor package in the form of a heating blanket.

Figure 8B:
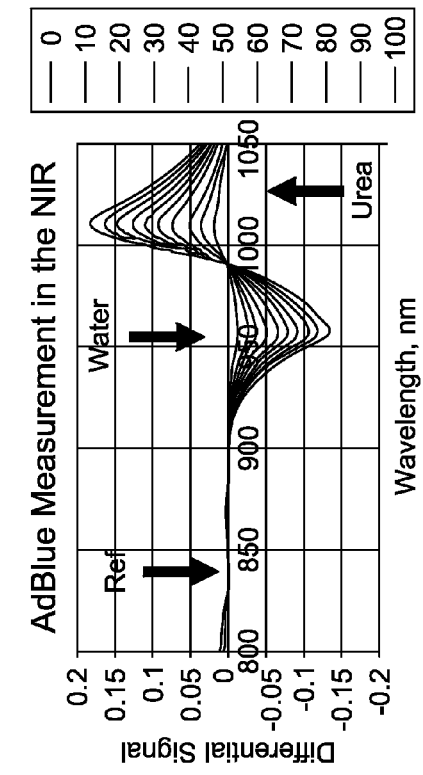
FIGS. 8A-8D are graphical representations of the absorption spectra of water and DEF, analytical wavelengths for water and urea, exemplary light-emitting diode (LED) wavelengths, and a resulting calibration function derived therefrom.
Figure 8D:
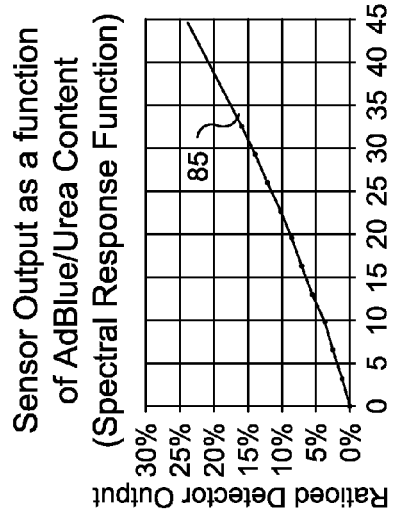
Figure 8A:
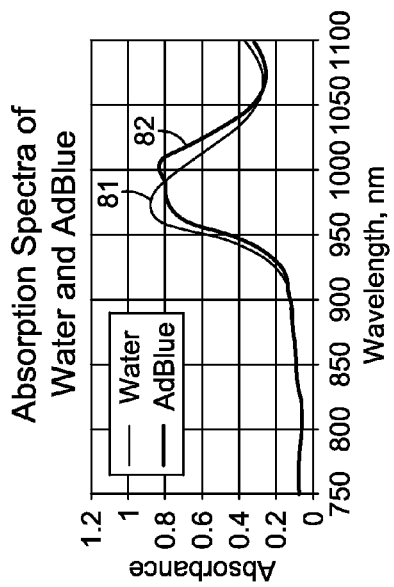
Figure 8C:
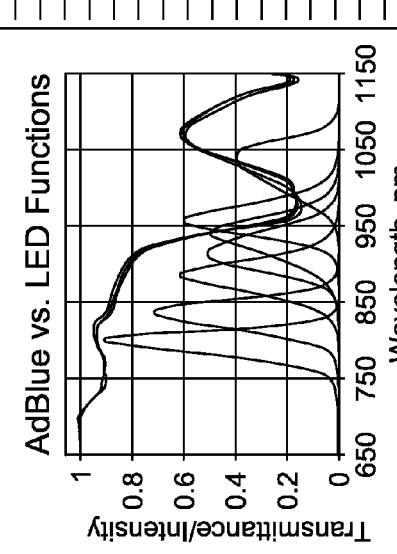

Referring generally to FIG. 8A, using embodiments of the sensors described herein in a simple binary fluid system, such as in a DEF system, the absorption spectrum of the two main components (i.e. water 81 and DEF 82) may be separated spectrally. Measurements of concentration are obtained by the use of two or more LEDs that represent the analytical wavelengths for the analysis. The wavelengths of these LEDs are indicated in FIGS. 8B and 8C, wherein analytical wavelengths for water, urea and a reference wavelength are defined. The measurement can be enhanced by performing the measurement as a differential, where the water response is referenced against the DEF response. Using normal spectral absorption calculations based on the absorption of the analytical wavelengths for water and urea referenced against a reference wavelength, a calibration function 85 for DEF can be derived (FIG. 8D).

Experiments performed over various operational temperature ranges indicate that both electronics and many fluids exhibit a temperature sensitivity that result in inaccuracies in measured parameters. According to one embodiment herein, this hysteresis can be modeled by observing the responses of the sensor with different temperature settings for the sensor immersed in various types of fluid. From these observations a series of response curves can be derived. Mathematical fitting has shown that these functions are reproducible and are easily fitted to a simple polynomial function. More specifically, both the fluid and the sensor temperature response functions can be represented by a simple $2^{nd}$ order polynomial. An exemplary calculation for performing this thermal modeling is outlined herein.

Figure 15:
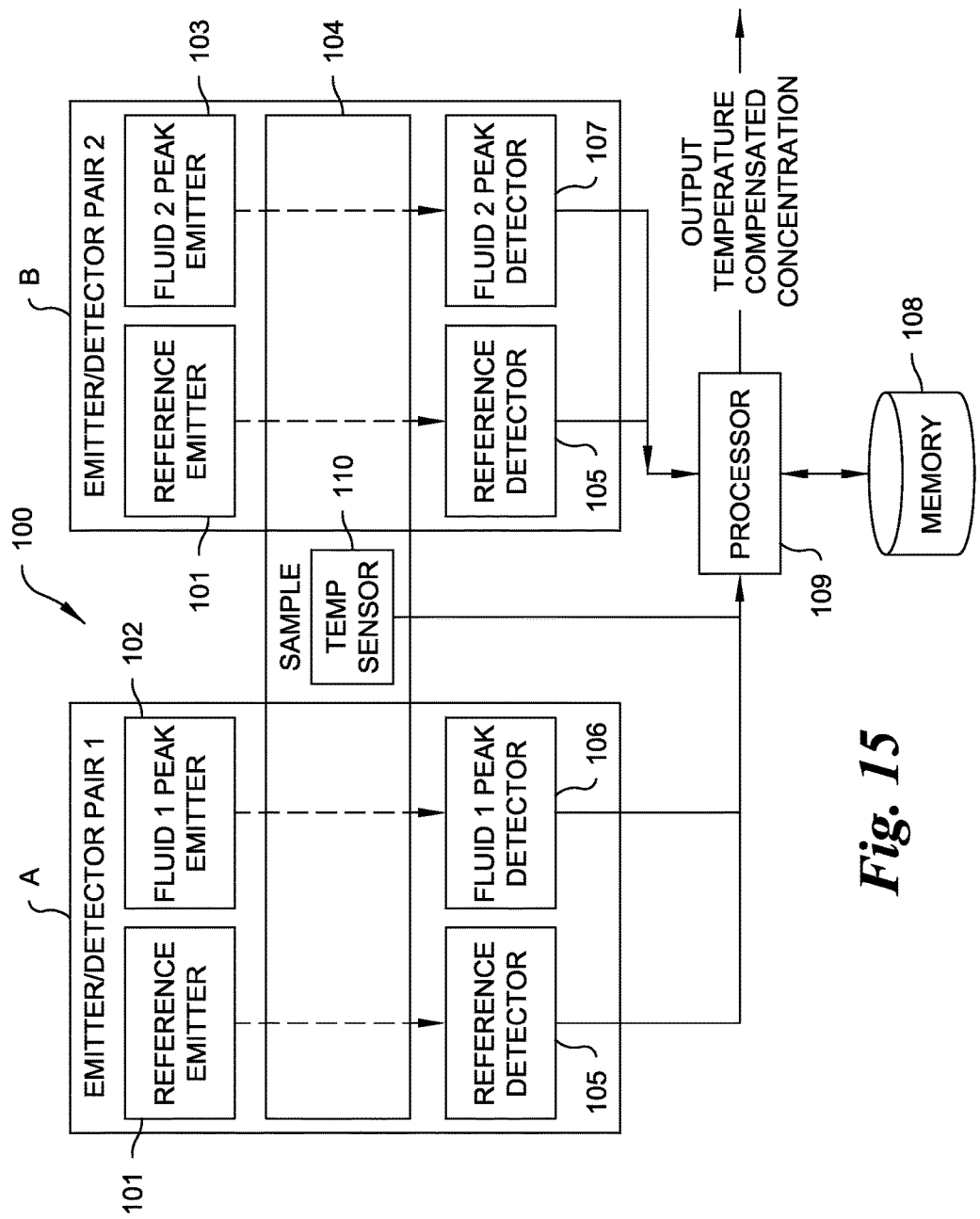
FIG. 15 is a schematic diagram illustrating a system for performing temperature compensated fluid measurements according to an embodiment of the present invention.

In FIG. 15, an LED-based optical sensor 100 is schematically illustrated and configured to measure the DEF composition of a fluid. Exemplary sensor 100 may comprise two optical packages A,B, each comprising two LEDs. Package A contains 810 nm and 970 nm wavelength LEDs 101,102, while package B contains 810 nm and 1050 nm wavelength LEDs 101,103. In the exemplary embodiment, there is an 810 nm LED 101 in each package because the 810 nm light is not affected by water or DEF and, as such, they can be used as a reference and may be employed to compensate for variations resulting from differences in path length. In this way, a ratio of "1050/810" represents the relative amount of 1050 nm light intensity compared to the 810 nm intensity. The same is true for an "970/810" ratio. Optical packages A,B further comprise respective reference detectors 105 responsive to the output of reference emitters 101, as well as detectors 106,107 responsive to emitters 102,103, respectively. Sensor 100 further comprises a processor 109 responsive to a temperature sensor 110 for measuring the temperature of a fluid 104 to be sampled, and for performing the below-described steps for calculating the composition of the fluid. Memory device 108 is provided for storing predetermined temperature to absorption/intensity ratios of DEF and water. More specifically, memory device 108 may store calibration data, including values of intensity of radiation transmitted through water at the reference frequency; the frequency corresponding to an absorption peak of water; the frequency corresponding to the absorption peak of DEF; values of intensity of radiation transmitted through DEF at the reference frequency; the frequency corresponding to an absorption peak of DEF; and the frequency corresponding to the absorption peak of DEF.

Figure 9:
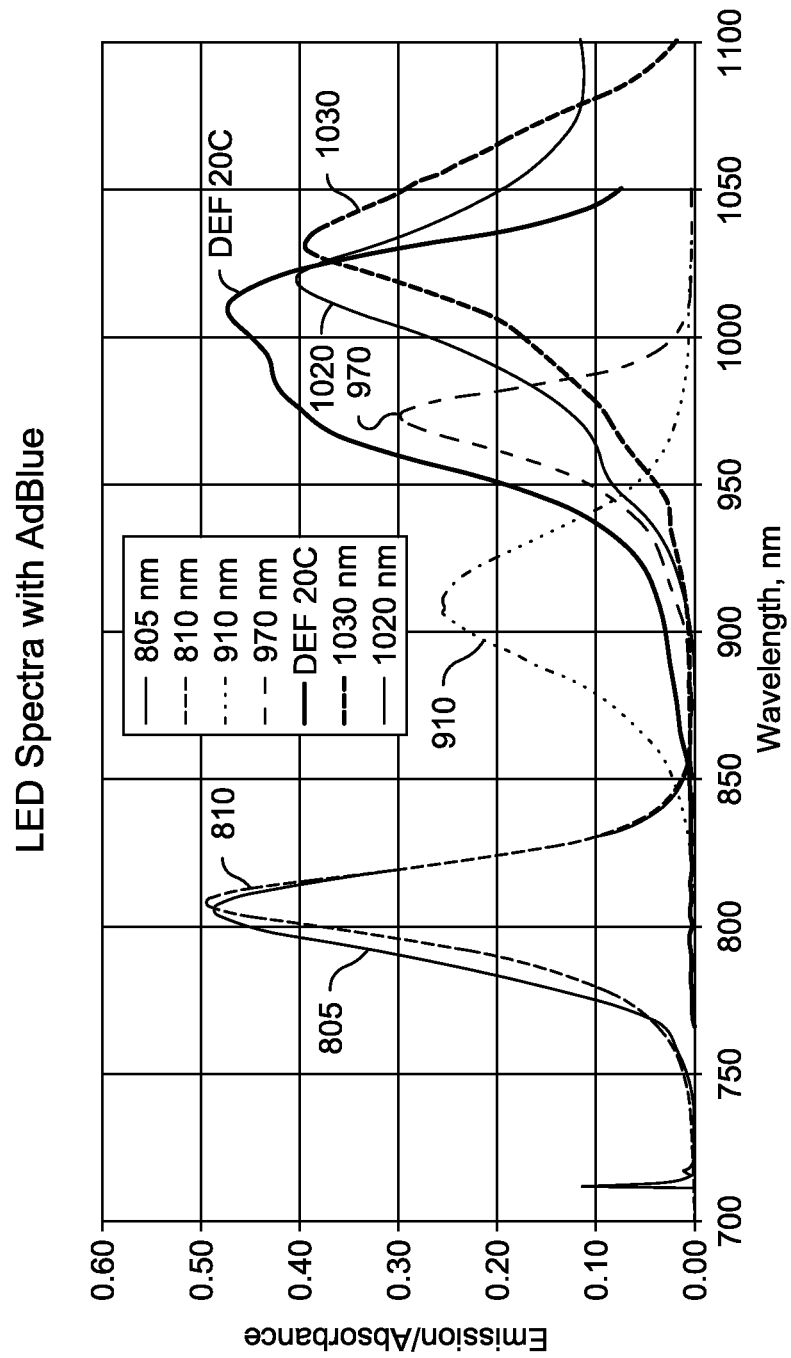
FIG. 9 is a graphical representation of an exemplary LED emission spectra and a DEF absorption spectra at 20 Celsius (C).

In operation, sensor 100 turns on one LED at a time in sequence, the light from the LED is transmitted through a specific volume of the DEF fluid. As the light traverses the fluid, certain chemical bonds in the fluid absorb energy at specific wavelengths of light. For example, FIG. 9 illustrates the LED emission spectra and the DEF (also called DEF interchangeably) absorption spectra at 20 C. As shown, the OH bond in water absorbs at 970 nm, while the NH bond in urea absorbs at about 1050 nm. By measuring the relative energy detected by the detector, the amount of absorbed light at these two wavelengths is measured, and by having a reference for each LED to normalize optical path variations, the concentration of urea in water can be calculated.

In practice, the nominal urea concentration in DEF is 32.5% as it provides the lowest freezing point; this concentration of urea in water is considered to be 100% DEF. Accordingly, an algorithm according to an embodiment of the present invention may use the 1050/970 absorption ratios of pure water to be 0% DEF and the 1050/970 absorption ratios of pure DEF to be 100% as endpoints in calibration:

DA(T) represents the difference between the scaled 1050 nm and 970 nm LEDs at a given temperature in pure DEF:

$$DA(T) = 1050/810B(DEF) - 970/810A(DEF)$$
$$= da2^*T2 + da1^*T + da0$$

DT(T) represents the difference between the scaled ratio of pure water, minus the scaled DEF ratio:

$$DT(T) = (1050/810B - 970/810A)W -$$
$$(1050/810B - 970/810A)DEF$$
$$= dt2^*T^2 + dt1^*T + dt0$$

A scaling term O(T) may be provided for normalizing the two 810 nm signals if needed:

$$O(T) = o2^*T^2 + o1(T) + 02$$

The 1050/970 absorption ratio of the "measured" fluid of unknown composition is then linearly scaled using the 0% to 100% ratios previously calibrated:

$$DM = 100^*O(T)^*1050raw/810Braw - 100^*970raw/810Araw$$

Finally, the DEF composition of the fluid can be calculated according to the following relationship:

$$\% DEF = 100^*((DT(T) + DA(T)) - DM/DT(T)$$

As absorption ratios are a strong function of temperature at various concentrations, the 0% and 100% set points may be adjusted for the actual temperature during measurements.

Figure 10:
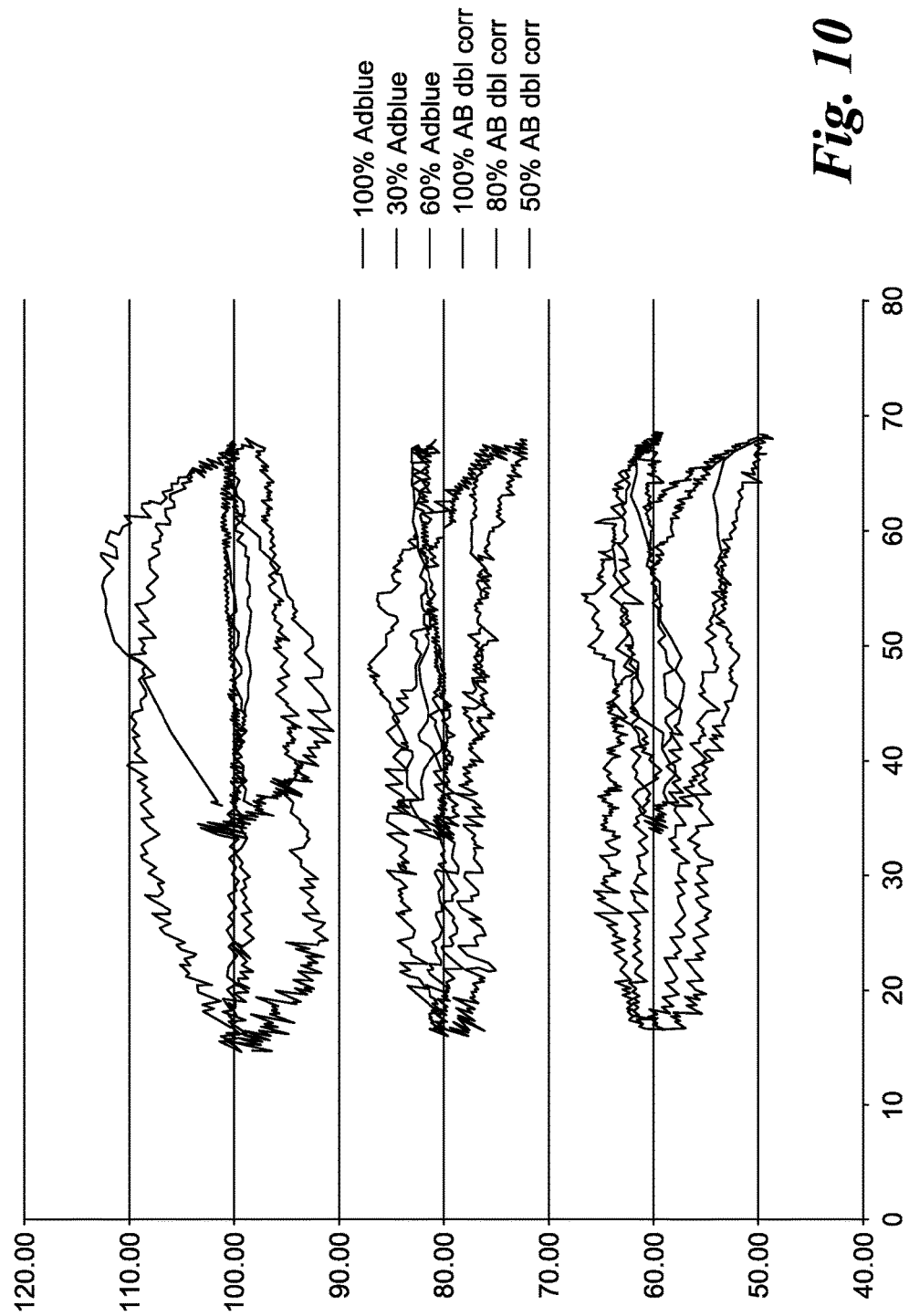
FIG. 10 shows a graphical representation of both temperature compensated and uncompensated measurements with various DEF concentrations.

The calculated DEF composition comprises a linear extrapolation, including a normalizing function for the 810 nm LED differences (O(T)), and is a function of the fluid temperature. FIG. 10 provides both temperature corrected and uncorrected outputs from an exemplary sensor, illustrating the functional benefits of the above-described temperature correction algorithm.

In determining concentration by an electronics package according to an embodiment, calibration data including temperature-dependent linear interpolation data between pure first fluid and pure second fluid intensity data may be stored in a memory device and accessed by a processor.

Figure 11:
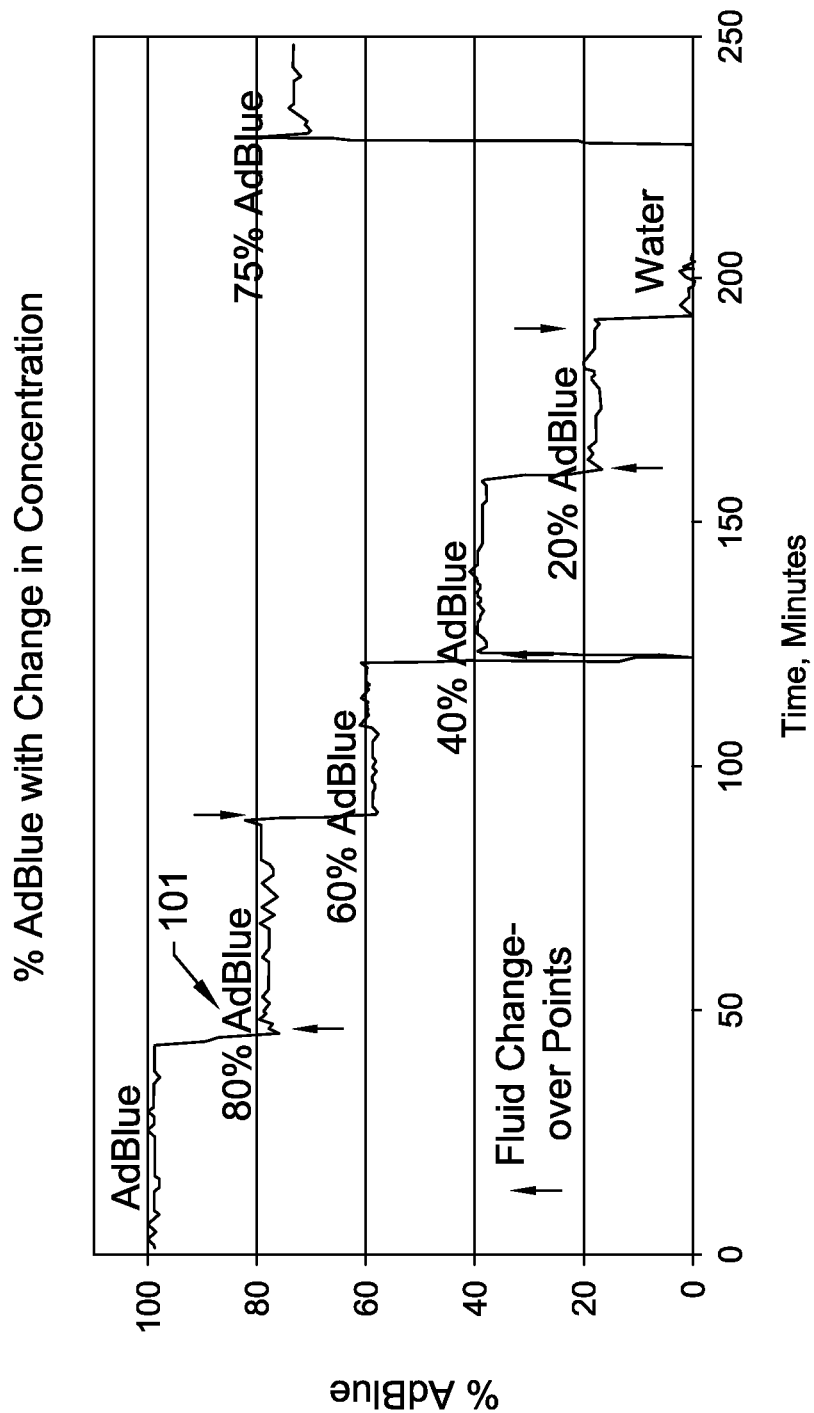
FIG. 11 is a graphical representation of an exemplary sensor output used to measure DEF concentrations.

Referring generally to FIG. 11, exemplary outputs of a sensor for changes in fluid concentration are shown. According to one embodiment of the present disclosure, using a control computer responsive to the output of one or more sensors, error codes can be generated that show the concentration being below a predetermined acceptable level. In the case of DEF this predetermined value 110 may be approximately 80%. Other errors codes that can be considered based on relative and/or absolute absorption responses of the LEDs include empty sensor, dirty sensor, dirty fluid and/or wrong fluid, as it pertains to the presence of coolant or fuel, for example.

Figure 12:
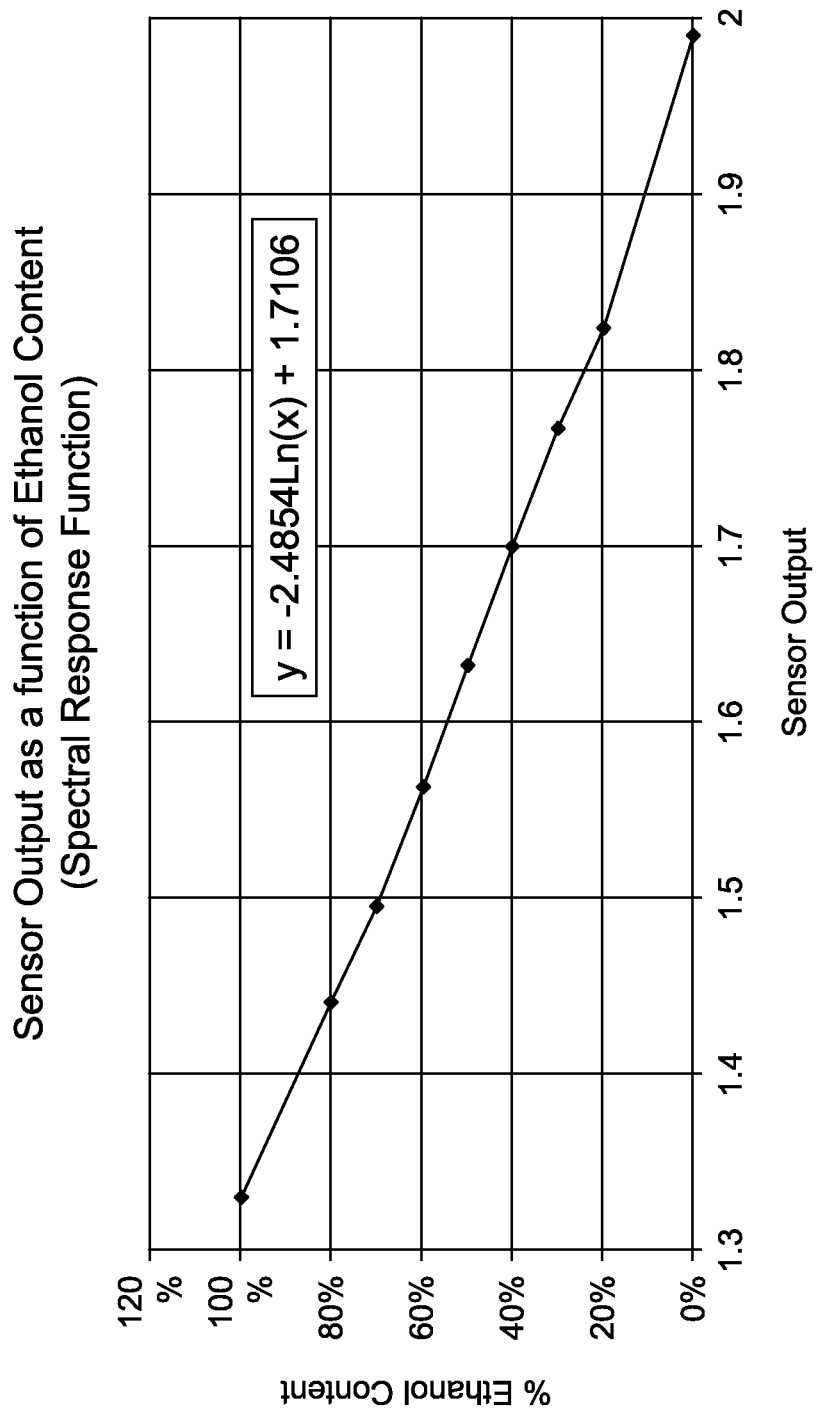
FIG. 12 is a graphical representation of the spectral response of Ethanol-Gasoline blends.
Figure 13:
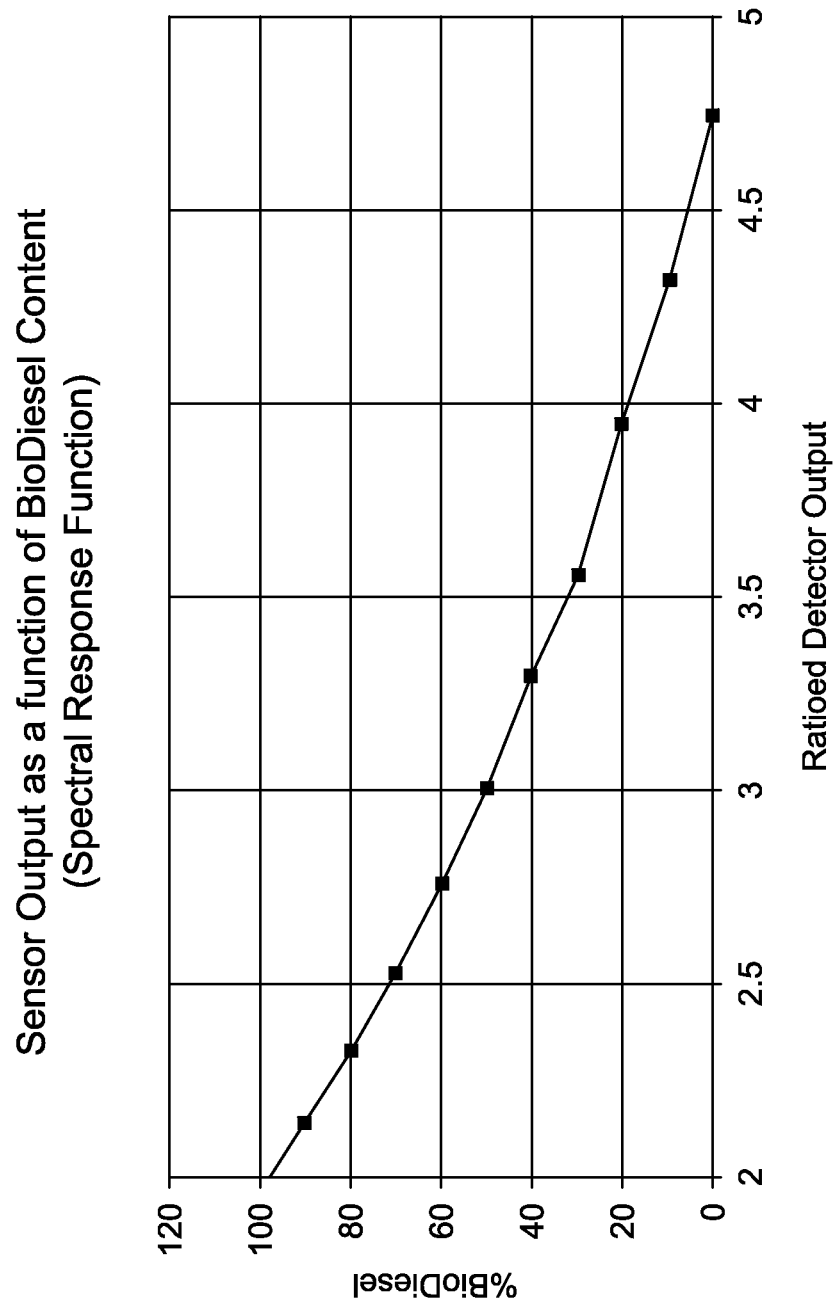
FIG. 13 is a graphical representation of the spectral response of Bio-Diesel-Diesel blends.

While the above-described embodiments of the present discloser have been described primarily in the context of an aqueous-based system, it should be understood that the applications of the sensors described herein are not limited to this fluid, and mixtures such as coolant blends can be considered. Also, non-aqueous systems can be considered, such as fuels. For example, the determination of ethanol content of gasoline-ethanol blends may be especially useful given today's use of flex-fuel applications. An example spectral response function for gasoline-ethanol systems is illustrated in FIG. 12. Likewise, another fuel system that can be measured by the quality/composition sensor is the amount of bio-diesel used in biodiesel blends. These blends involve mixtures with petroleum diesel, where the biodiesel content may range from zero, B0, to 5% B5, to 100% B100. With the use of, for example, a 6-LED system, the sensor can be adapted to monitoring bio-diesel blends. A spectral response function for this system is illustrated in FIG. 13.

Example applications for the embodiments described herein include the following:
a) Quality assessment and composition monitoring of diesel emission fluid (aka DEF and AdBlue®),
b) Composition of blended fuels, including bio fuels, such as biodiesel blends and gasoline-ethanol blends,
c) Monitoring of gases and vapors, with an example of NOx components in exhaust and blow-by gases,
d) the monitoring of oxidation/acidity in transmission and other lubricating oils,
e) the measurement of oil condition in gasoline and natural gas-fired engines based on the formation of oxidation and nitro-oxidation products,
f) the measurement of dispersed water (elevated levels) in hydraulic and lubrication oil systems,
g) the measurement of turbidity, which can result from water, air entrainment and/or particulates or other insoluble materials in functional fluids,
h) the measurement of coolant condition, based on color, composition and turbidity,
i) the measurement of marker materials for fluid compatibility, usage and/or condition (color markers added to indicate chemical changes), including fuel markers,
j) the monitoring of battery acid condition (acid strength), based on a color indicator, etc.
k) rear axle fluid monitoring for level and breakdown l) the measurement of fluid density based on refractive index Exemplary embodiments of the present disclosure may include:

A urea quality sensor (UQS): A sensor based on optical transmission measurements with a path length defined by the spectral method of measurement. The fluid is considered to be a two-component system, involving water and urea as the designated and only ingredients, and where spectral measurement is based on the unique absorptions of the amino functionality of the urea, $CO(NH_2)_2$, and the hydroxyl functionality of the water, $H_2O$ or HO—H. Those of skill in the art of optical and vibrational spectroscopy will recognize that these are well-defined and unique functionalities and can be measured in at least five regions of the total spectral range from the visible to the mid-infrared. For convenience and in-line with the goal of defining a cost effective solution the measurement region selected is the short wave near infrared, where wavelengths are selected from 970 nm to 1050 nm for the measurement of these two functionalities. These wavelengths may be monitored by LEDs with nominal outputs at 970 nm and 1050 nm. As set forth above, the measurement can be maximized for dynamic range by a differential measurement, referenced to an internal standard wavelength at 810 nm to provide a calibration function. This can be done by consideration that there is only two components that are supposed to be in the fluid.

Blend composition for bio-fuels: There are two common usages of bio-fuels for automotive and combustion engine application and those are for biodiesel (fatty acid methyl esters or FAME) and for ethanol. In both cases the fuel is used as a blend, with standard, hydrocarbon diesel for biodiesel, and with standard gasoline for ethanol. These are sometimes designated as B-blends (B0 to B100) for biodiesel and E-blends (E0 to E100) for ethanol blends, where the number designates the bio-fuel content. Like the previous application for DEF infrared spectral signatures can be defined that occurred repeatedly throughout the near infrared and mid-infrared, and that these can be conveniently measured in the short wave near infrared. The measurement for ethanol in gasoline is similar to that of DEF, where two analytical wavelengths, defining the hydrocarbon CH and the ethanol OH can be selected and used relative to a common reference at 810 nm (no absorptions at this point). The measurement of the biodiesel is a more complex and requires more wavelengths to be used. In this case CH information is used for both components, in one case the CH associated with the hydrocarbon is used and in the other the CH from the carbon adjacent to the ester functionality is used.

Monitoring of gases and vapors: Optical spectroscopy can be used for the detection and composition monitoring of gases and vapors, and these measurements can be performed throughout the entire spectral region from the UV to the mid-infrared. At low concentration a longer path length is required and an example of the extension of the path is provided in the retro-reflective configuration of the sensor, as illustrated in FIG. 4B. There is a desire to have a low-cost measurement of NOx. This may be accomplished in the UV by the use of UV LEDs, for monitoring NO and NOx. This measurement mirrors the method used industrially for the gas phase measurement of these two NOx emission components.

Monitoring density via refractive index: Refractive index varies as function of material composition and concentration. These correlate well to density changes in a fluid. Both density and viscosity are used for fluid systems such as DEF for a bulk measurement of material concentration, with urea being the relevant component in DEF. Several commercial sensors utilize density or density related measurements to monitor changes in urea concentration of DEF. The optical sensor described in U.S. Pat. No. 7,339,657 uses a refractive sensor tip that can be adapted to measure refractive index. Changes in the index are monitored as changes in optical attenuation, and these can be correlated, by calibration, to changes in urea content. This role for the sensor is not limited to the measurement of DEF concentration, and the sensor may be applied to other combinations of fluids, including fuel blends and coolant mixtures.

Monitoring of oxidation and nitration products in gasoline and gas-fired engines: It has been satisfactorily been demonstrated that the optical spectrum can model and trend both oxidation and nitro-oxidation if multiple wavelengths are monitored in the visible and short wave NIR regions. As the oil oxidizes and degrades, extended double bond structures are formed as part of aldol condensations that take place in the degradation pathway. These materials eventually become the insoluble organic sludge that separates from the oil after extended use. As the extended double-bond structures form, the absorption wavelength of these materials shifts to the red end of the spectrum, and eventually into the short-wave NIR. They may be tracked by monitoring the visible (green, yellow, red) and the NIR wavelengths. Also, the formation of nitro components, from the NOx components may also be tracked in the visible.

Monitoring of oxidation and acid number in automatic transmissions: The red dye used in Dexron automatic transmission fluids can be demonstrated to act as an acid-base indicator, reflecting the condition and the acidity of the fluid during use. The acid number of transmissions used in buses is an issue relative to warranty claims. An on-board sensor capable of modeling acid value based on the visible monitoring of the dye can provide an early warning to unacceptable acid numbers (relative to warranty). A sensor configured in a similar manner to the oxidation sensor described can be adequate, but probably without the need for the NIR channel.

While the foregoing invention has been described with reference to the above-described embodiment, various modifications and changes can be made without departing from the spirit of the invention. Accordingly, all such modifications and changes are considered to be within the scope of the appended claims. Accordingly, the specification and the drawings are to be regarded in an illustrative rather than a restrictive sense. The accompanying drawings that form a part hereof, show by way of illustration, and not of limitation, specific embodiments in which the subject matter may be practiced. The embodiments illustrated are described in sufficient detail to enable those skilled in the art to practice the teachings disclosed herein. Other embodiments may be utilized and derived therefrom, such that structural and logical substitutions and changes may be made without departing from the scope of this disclosure. This Detailed Description, therefore, is not to be taken in a limiting sense, and the scope of various embodiments is defined only by the appended claims, along with the full range of equivalents to which such claims are entitled.

Such embodiments of the inventive subject matter may be referred to herein, individually and/or collectively, by the term "invention" merely for convenience and without intending to voluntarily limit the scope of this application to any single invention or inventive concept if more than one is in fact disclosed. Thus, although specific embodiments have been illustrated and described herein, it should be appreciated that any arrangement calculated to achieve the same purpose may be substituted for the specific embodiments shown. This disclosure is intended to cover any and all adaptations of variations of various embodiments. Combinations of the above embodiments, and other embodiments not specifically described herein, will be apparent to those of skill in the art upon reviewing the above description.

What is claimed is:

1. An optical spectral sensing device for determining at least one property of a fluid, the device comprising:
    an elongated body having a first and a second end;
    an optical emitter at the first end of the body and oriented to emit radiation toward the second end of the body;
    an optical detector at the second end of the body oriented to detect radiation emitted by the optical emitter, and configured to output a signal representative of the detected radiation; and
    an electronics package for providing energy for the optical emitter and for receiving the signal representative of the detected radiation generated by the optical detector,
    wherein the electronics package is configured to, when the first end is submerged in a fluid and the second end is above the fluid, based on the signal generated by the detector, output at least one value indicative of the fluid depth, and
    wherein the device is configured to determine fluid depth responsive to absorption of emitted radiation by the fluid.

2. The optical sensing device of claim 1, wherein the electronics package further comprises a memory device configured to store a predetermined absorption vs. depth relationship for the fluid to be measured, and wherein the electronics package is configured to determine a value indicative of the light absorbed by the fluid, and output at least one value indicative of the fluid depth via a comparison of the value indicative of absorbed light and the predetermined absorption vs. depth relationship.

3. The optical sensing device of claim 1, wherein the electronics package is further configured to output at least one value indicative of the fluid composition.

4. The optical sensing device of claim 1, wherein the elongated body is porous.

5. The optical sensing device of claim 4, wherein the porous body is hollow, and the optical emitter and optical detector are mounted to transmit and receive radiation within a hollow interior of the porous body.

6. The optical sensing device of claim 1, wherein the optical emitter comprises a solid-state optical emitter.

7. The optical sensing device of claim 6, wherein the optical emitter comprises at least one light-emitting diode (LED).

8. The optical sensing device of claim 1, wherein the optical detector comprises a solid-state optical detector.

9. The optical sensing device of claim 8, wherein the optical detector comprises a silicon photodiode.

10. The optical sensing device of claim 1, wherein the optical detector is integrally formed on an electronic control board.

11. A method for determining the depth of a volume of fluid, comprising:
    radiating energy through a volume of fluid via an optical emitter arranged at a first end of a first end of an elongated body and oriented to emit radiation toward a second end of the elongated body;
    receiving the energy radiated by the optical emitter through the volume of fluid at an optical detector arranged at the second end of the elongated body;
    calculating, by an electronics package, a value indicative of the energy absorbed by the fluid via a comparison between the energy radiated by the optical emitter and the energy received by the optical detector, and
    determining, by the electronics package, the depth of the fluid based at least in part on the calculated value indicative of the energy absorbed by the fluid.

12. The method of claim 11, wherein the step of determining the depth of the fluid comprises comparing the calculated value indicative of absorbed energy to a predetermined value to determine the depth of the volume of fluid.

13. The method of claim 11, wherein the elongated body comprises a porous body, and the optical emitter and optical detector are mounted to transmit and receive energy within a hollow interior of the porous body.

14. The method of claim 13, wherein at least one of the ends of the porous body is submerged in the volume of fluid simultaneously with the steps of radiating and receiving energy.

15. The method of claim 11, further comprising determining composition of the fluid by analyzing the energy received at the optical detector.

* * * * *